United States Patent
Takenaka et al.

(10) Patent No.: US 8,167,486 B2
(45) Date of Patent: *May 1, 2012

(54) IMAGING SYSTEM AND DRIVING METHOD THEREOF

(75) Inventors: Katsuro Takenaka, Honjo (JP); Tadao Endo, Honjo (JP); Toshio Kameshima, Kumagaya (JP); Tomoyuki Yagi, Honjo (JP); Keigo Yokoyama, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/940,444

(22) Filed: Nov. 5, 2010

(65) Prior Publication Data

US 2011/0044430 A1 Feb. 24, 2011

Related U.S. Application Data

(62) Division of application No. 12/328,302, filed on Dec. 4, 2008, now Pat. No. 7,850,367, which is a division of application No. 11/751,686, filed on May 22, 2007, now Pat. No. 7,476,027.

(30) Foreign Application Priority Data

Jun. 16, 2006 (JP) ................................ 2006-167876

(51) Int. Cl.
 G01D 18/00 (2006.01)
 H05G 1/58 (2006.01)
(52) U.S. Cl. ......................... 378/207; 378/98.7; 378/116
(58) Field of Classification Search .................. 378/98.7, 378/114, 115, 116, 207
 See application file for complete search history.

(56) References Cited

U.S. PATENT DOCUMENTS

| | | | |
|---|---|---|---|
| 5,617,461 A | 4/1997 | Schreiner | 378/98.5 |
| 6,859,513 B2 | 2/2005 | Sako | 378/16 |
| 6,952,015 B2 | 10/2005 | Kameshima | 250/370.11 |

(Continued)

FOREIGN PATENT DOCUMENTS

JP 8-116044 5/1996

(Continued)

OTHER PUBLICATIONS

Japanese Office Action dated May 24, 2011, issued in Japanese counterpart, Japanese Patent Application No. 2006-167876, with translation of substance.

*Primary Examiner* — Glen Kao

(74) *Attorney, Agent, or Firm* — Fitzpatrick, Cella, Harper & Scinto

(57) ABSTRACT

When a gain correction is performed for the radiographed object image, the acquisition of the object image having a high grade quality and no artifact is realized. For that purpose, an image storing unit is provided for storing an image for correction radiographed based on conditions set with the table in a state in which no object exists to each operation modes of the plurality of operation modes; and an image processing unit is provided for performing a gain correction processing of the radiographed object image and performs the gain correction processing of the radiographed object image obtained based on the conditions set in the table of the operation mode selected by the selecting unit in a state in which the object exists using a corresponding image for correction extracted from the image storage unit based on the operation mode selected by the selecting unit.

8 Claims, 14 Drawing Sheets

U.S. PATENT DOCUMENTS

| | | | |
|---|---|---|---|
| 6,952,464 B2 | 10/2005 | Endo | 378/98.11 |
| 6,985,555 B2 | 1/2006 | Endo | 378/98.11 |
| 7,002,157 B2 | 2/2006 | Kameshima | 250/370.11 |
| 7,012,260 B2 | 3/2006 | Endo | 250/370.11 |
| 7,138,639 B2 | 11/2006 | Kameshima | 250/370.11 |
| 7,154,099 B2 | 12/2006 | Endo | 250/370.11 |
| 7,227,926 B2 | 6/2007 | Kameshima et al. | 378/98.9 |
| 7,408,167 B2 | 8/2008 | Kameshima et al. | 250/370.09 |
| 7,421,063 B2 | 9/2008 | Takenaka et al. | 378/98.2 |
| 7,476,027 B2 | 1/2009 | Takenaka et al. | 378/207 |
| 7,532,706 B2 | 5/2009 | Kameshima et al. | 378/98 |
| 7,629,587 B2 | 12/2009 | Yagi et al. | 250/370.15 |
| 7,850,367 B2 * | 12/2010 | Takenaka et al. | 378/207 |
| 2004/0066900 A1 | 4/2004 | Motoki | 378/116 |
| 2005/0109927 A1 | 5/2005 | Takenaka et al. | 250/252.1 |
| 2005/0199834 A1 | 9/2005 | Takenaka et al. | 250/580 |
| 2005/0200720 A1 | 9/2005 | Kameshima et al. | 348/220.1 |
| 2005/0220269 A1 | 10/2005 | Endo et al. | 378/114 |
| 2005/0264665 A1 | 12/2005 | Endo et al. | 348/308 |
| 2006/0104417 A1 | 5/2006 | Kameshima et al. | 378/98 |
| 2006/0119719 A1 | 6/2006 | Kameshima | 348/308 |
| 2006/0192130 A1 | 8/2006 | Yagi | 250/370.14 |
| 2006/0289774 A1 | 12/2006 | Endo et al. | 250/370.09 |
| 2007/0040099 A1 | 2/2007 | Yokoyama et al. | 250/208.1 |
| 2007/0069144 A1 | 3/2007 | Kameshima | 250/370.09 |
| 2007/0080299 A1 | 4/2007 | Endo et al. | 250/370.09 |
| 2007/0096030 A1 | 5/2007 | Li et al. | 250/370.11 |
| 2007/0125952 A1 | 6/2007 | Endo et al. | 250/369 |
| 2007/0131843 A1 | 6/2007 | Yokoyama et al. | 250/205 |
| 2007/0183573 A1 | 8/2007 | Kameshima et al. | 378/98.9 |
| 2007/0210258 A1 | 9/2007 | Endo et al. | 250/370.09 |
| 2008/0011958 A1 | 1/2008 | Endo et al. | 250/370.08 |
| 2008/0013686 A1 | 1/2008 | Kameshima et al. | 378/98 |
| 2008/0029688 A1 | 2/2008 | Yagi et al. | 250/208.1 |
| 2008/0054182 A1 | 3/2008 | Yokoyama et al. | 250/370.09 |
| 2008/0083876 A1 | 4/2008 | Endo et al. | 250/369 |
| 2009/0294679 A1 | 12/2009 | Yagi et al. | 250/370.09 |
| 2010/0046711 A1 | 2/2010 | Kameshima et al. | 378/98.8 |

FOREIGN PATENT DOCUMENTS

| | | |
|---|---|---|
| JP | 2006-020714 | 1/2006 |
| JP | 2006-068512 | 3/2006 |

* cited by examiner

| | | X-RAY GENERATOR | | | | | X-RAY IMAGING APPARATUS |
|---|---|---|---|---|---|---|---|
| | | IRRADIATION MODES | TUBE VOLTAGE [kVp] | TUBE CURRENT [mA] | IRRADIATION TIME [ms] | GAIN | DRIVING MODES |
| STILL IMAGE RADIOGRAPHING MODE | LOW TUBE VOLTAGE | NORMAL | 50 | 125 | 50 | 1 | STILL IMAGE DRIVE |
| | MEDIUM TUBE VOLTAGE | NORMAL | 80 | 63 | 50 | 1 | STILL IMAGE DRIVE |
| | HIGH TUBE VOLTAGE | NORMAL | 140 | 40 | 50 | 1 | STILL IMAGE DRIVE |
| MOVING IMAGE RADIOGRAPHING MODE | 1x1 PIXELS ADDITION — LOW TUBE VOLTAGE | PULSE | 50 | 125 | 10 | 5 | MOVING IMAGE DRIVE (PIXEL NON-ADDITION) |
| | 1x1 PIXELS ADDITION — MEDIUM TUBE VOLTAGE | PULSE | 80 | 63 | 10 | 5 | MOVING IMAGE DRIVE (PIXEL NON-ADDITION) |
| | 1x1 PIXELS ADDITION — HIGH TUBE VOLTAGE | PULSE | 140 | 40 | 10 | 5 | MOVING IMAGE DRIVE (PIXEL NON-ADDITION) |
| | 2x2 PIXELS ADDITION — LOW TUBE VOLTAGE | PULSE | 50 | 125 | 2.5 | 5 | MOVING IMAGE (2x2 PIXELS ADDITION) DRIVE |
| | 2x2 PIXELS ADDITION — MEDIUM TUBE VOLTAGE | PULSE | 80 | 63 | 2.5 | 5 | MOVING IMAGE (2x2 PIXELS ADDITION) DRIVE |
| | 2x2 PIXELS ADDITION — HIGH TUBE VOLTAGE | PULSE | 140 | 40 | 2.5 | 5 | MOVING IMAGE (2x2 PIXELS ADDITION) DRIVE |
| | 4x4 PIXELS ADDITION — LOW TUBE VOLTAGE | PULSE | 50 | 40 | 2 | 5 | MOVING IMAGE (4x4 PIXELS ADDITION) DRIVE |
| | 4x4 PIXELS ADDITION — MEDIUM TUBE VOLTAGE | PULSE | 80 | 20 | 2 | 5 | MOVING IMAGE (4x4 PIXELS ADDITION) DRIVE |
| | 4x4 PIXELS ADDITION — HIGH TUBE VOLTAGE | PULSE | 140 | 10 | 2 | 5 | MOVING IMAGE (4x4 PIXELS ADDITION) DRIVE |

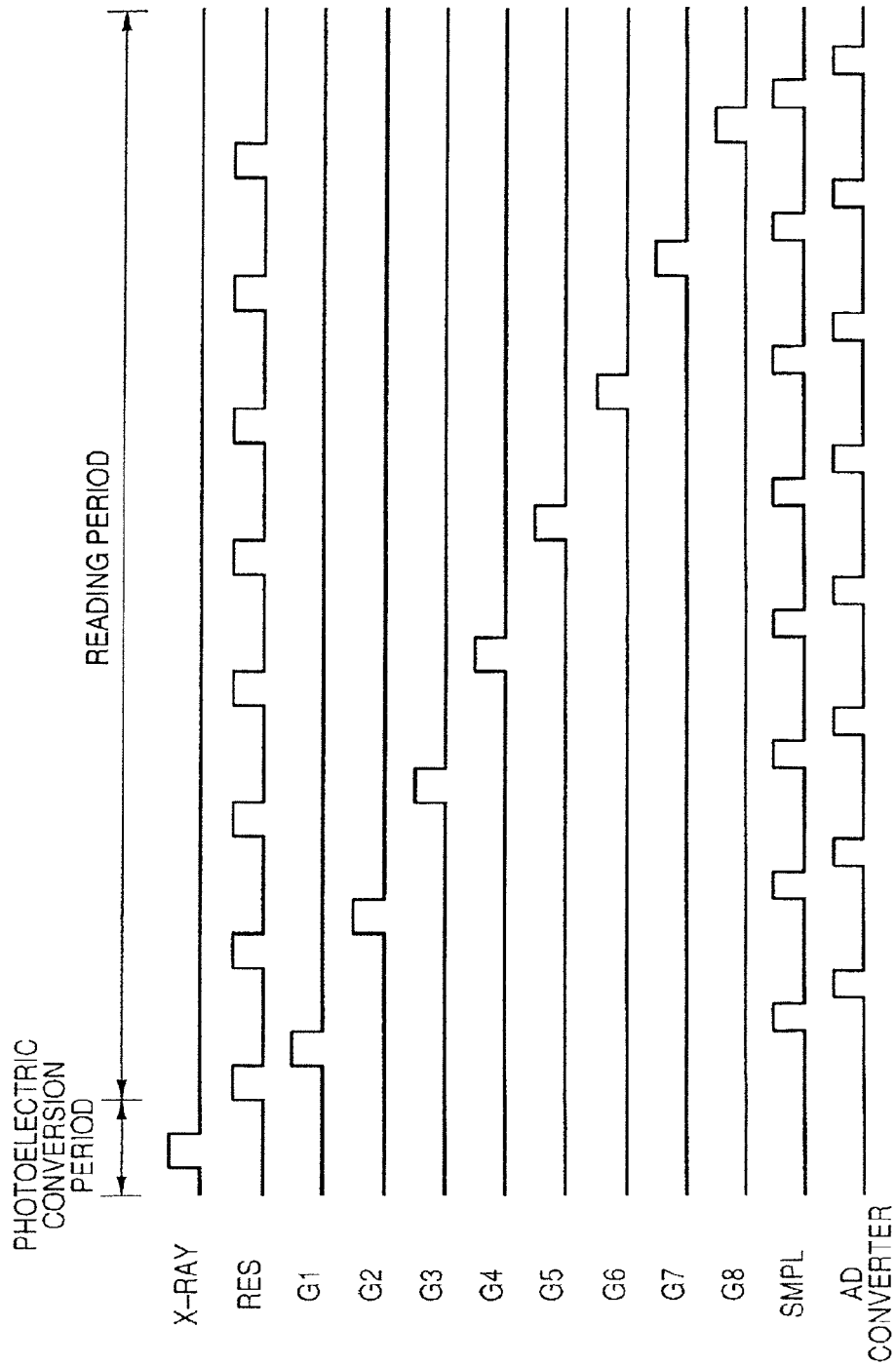

FIG. 10

| | | X-RAY GENERATOR | | | | | X-RAY IMAGING APPARATUS |
|---|---|---|---|---|---|---|---|
| | | IRRADIATION MODES | TUBE VOLTAGE [kVp] | TUBE CURRENT [mA] | IRRADIATION TIME [ms] | GAIN | LPF Fc [Hz] | DRIVING MODES |
| STILL IMAGE RADIOGRAPHING MODE | LOW TUBE VOLTAGE | NORMAL | 50 | 125 | 50 | 1 | 20 | STILL IMAGE DRIVE |
| | MEDIUM TUBE VOLTAGE | NORMAL | 80 | 63 | 50 | 1 | 20 | STILL IMAGE DRIVE |
| | HIGH TUBE VOLTAGE | NORMAL | 140 | 40 | 50 | 1 | 20 | STILL IMAGE DRIVE |
| MOVING IMAGE RADIOGRAPHING MODE | 1×1 PIXELS ADDITION — LOW TUBE VOLTAGE | PULSE | 50 | 125 | 10 | 5 | 200 | MOVING IMAGE DRIVE (PIXEL NON-ADDITION) |
| | 1×1 PIXELS ADDITION — MEDIUM TUBE VOLTAGE | PULSE | 80 | 63 | 10 | 5 | 200 | MOVING IMAGE DRIVE (PIXEL NON-ADDITION) |
| | 1×1 PIXELS ADDITION — HIGH TUBE VOLTAGE | PULSE | 140 | 40 | 10 | 5 | 200 | MOVING IMAGE DRIVE (PIXEL NON-ADDITION) |
| | 2×2 PIXELS ADDITION — LOW TUBE VOLTAGE | PULSE | 50 | 125 | 2.5 | 5 | 200 | MOVING IMAGE (2×2 PIXELS ADDITION) DRIVE |
| | 2×2 PIXELS ADDITION — MEDIUM TUBE VOLTAGE | PULSE | 80 | 63 | 2.5 | 5 | 200 | MOVING IMAGE (2×2 PIXELS ADDITION) DRIVE |
| | 2×2 PIXELS ADDITION — HIGH TUBE VOLTAGE | PULSE | 140 | 40 | 2.5 | 5 | 200 | MOVING IMAGE (2×2 PIXELS ADDITION) DRIVE |
| | 4×4 PIXELS ADDITION — LOW TUBE VOLTAGE | PULSE | 50 | 40 | 2 | 5 | 200 | MOVING IMAGE (4×4 PIXELS ADDITION) DRIVE |
| | 4×4 PIXELS ADDITION — MEDIUM TUBE VOLTAGE | PULSE | 80 | 20 | 2 | 5 | 200 | MOVING IMAGE (4×4 PIXELS ADDITION) DRIVE |
| | 4×4 PIXELS ADDITION — HIGH TUBE VOLTAGE | PULSE | 140 | 10 | 2 | 5 | 200 | MOVING IMAGE (4×4 PIXELS ADDITION) DRIVE |

<X-RAY RADIOGRAPHING AT 80kVp>

<X-RAY RADIOGRAPHING AT 60kVp>

<OBJECT IMAGE DERIVED AT 80kVp/
IMAGE FOR GAIN CORRECTION AT 60KkVp>

IMAGING SYSTEM AND DRIVING METHOD THEREOF

RELATED APPLICATIONS

This is a divisional of application Ser. No. 12/328,302, filed Dec. 4, 2008, which is a divisional of application Ser. No. 11/751,686, filed May 22, 2007 (now U.S. Pat. No. 7,476,027, issued Jan. 13, 2009), claims benefit of both of those applications under 35 U.S.C. §120, and claims benefit under 35 U.S.C. §119 of Japanese patent application no. 2006/167876, filed Jun. 16, 2006. The entire contents of each of the three mentioned prior applications are incorporated herein by reference.

BACKGROUND OF THE INVENTION

1. Field of the Invention

The present invention relates to a radiation imaging system for radiographing a radiation image of an object and a driving method thereof.

2. Description of the Related Art

In general, a demand for digitalization of an x-ray image in the hospital has been recently increasing. In reality, a radiation imaging apparatus such as, for example, FPD (Flat Panel Detector) has began to be used, in which an x-ray dosage is converted into electric signals by using a solid state imaging device in which x-ray detection elements (conversion elements) are disposed in a two-dimensional array pattern instead of a film.

In this X-ray imaging apparatus, since an X-ray image can be replaced by digital information, the image information can be transferred far away and instantaneously and this provides the advantage of being able to receive a sophisticated diagnosis comparable to a university hospital in the heart of the city, while being far away. Further, there is also the advantage of being able to save a storing space of the film in the hospital in case the film is not used. In future, if an excellent image processing technology can be introduced, an automatic diagnosis using a computer without an intermediary of a radiologist can be expected with great hopes.

In recent years, a radiation imaging apparatus has been put to practical use, in which an amorphous silicon thin film semiconductor is used for the solid state imaging device so as to radiograph a static image. Specifically, by using the manufacturing technology of the amorphous silicon thin film semiconductor, the radiation imaging apparatus comprising a solid state imaging device enlarged in its area exceeding 40 cm square to cover the size of human chest regions has been realized. This radiation imaging apparatus, because of relative easiness of its manufacturing process, is expected to provide an inexpensive apparatus in future. Moreover, since the amorphous silicon can be manufactured on a thin glass plate below 1 mm, it has an advantage of being able to make the thickness extremely thin as a detector. Such a radiation imaging apparatus, for example, is disclosed in Japanese Patent Application Laid-Open No. H08-116044.

Further, more recently, development of radiographing a moving image is underway in such a radiation imaging apparatus. If such a radiation imaging apparatus can be manufactured at a moderate price, the still image and moving image can be radiographed by the same one set, so that popularization of the apparatus can be expected in many hospitals.

SUMMARY OF THE INVENTION

When a moving image is radiographed by using the radiation imaging apparatus, as compared to the still image, the shortening of read time (quickening a frame rate) and the improvement of a S/N cause a problem. Hence, when the moving image is radiographed, a driving generally referred to as <pixel addition> is performed. Usually, a single pixel is read as one pixel (hereinafter, this one pixel is referred to as <unit pixel>), whereas, in the pixel addition, a plurality of pixels is put together and read as one pixel (hereinafter, this one pixel is referred to as <plural pixel>).

Next, by using circuit diagrams shown in FIGS. 11 and 12, the pixel addition will be described.

A technique for the pixel addition is variously considered. For example, this includes a technique in which two pieces of gate wiring are turned on at the same time, and as shown in FIG. 11, an analogue signal is subjected to the pixel addition before the AD conversion of an AD converter, and a technique in which, as shown in FIG. 12, the digital signal is added after the AD conversion. In the case of the former, since the analogue signal is added, and after that, the A/D conversion is performed, the data amount for the AD conversion is reduced, and the read time can be shortened. In contrast to this, in the case of the later, since the analogue signals are all AD-converted into digital signals, and then, the digital signals are added, the read time takes long. Further, as compared to the addition of the digital signals, the addition of the analogue signals is small in noise and high in S/N.

A quantum noise of the X-ray shown in FIGS. 11 and 12 is taken as <X-RAY>, and a shot noise of dark current of the conversion element is taken as <Senser>. Further, when a noise of a readout circuit unit (AMP) shown in FIGS. 11 and 12 is taken as <AMP> and a noise of the AD converter as <AD>, a total of noises can be determined by a sum of squares.

Specifically, the total noises by the analogue addition of FIG. 11 are shown by the following formula. 4×4

·Analogue addition noise=$\sqrt{\{(2\text{X-RAY})^2+(2\text{Senser})^2+(\text{AMP})^2+(\text{AD})^2\}}$ As shown in the above described formula, in the case of the analogue addition, the quantum noise <X-RAY> of the X-Ray and the noise <Senser> of the conversion element become ($\sqrt{2}$ times).

Further, a total of noises by the digital addition of FIG. 12 are shown by the following formula.

·Digital addition noise=$\sqrt{\{(2\text{X-RAY})^2+(2\text{Senser})^2+(2\text{AMP})^2+(2\text{AD})^2\}}$.

As shown in the above described formula, in the case of the digital addition, all the noises become ($\sqrt{2}$) times, and as compared to the case where the analogue signal is added, the noise becomes large.

Further, since an amount of the signal becomes twofold both for the analogue addition and the digital addition, the digital addition rather than the analogue addition has the S/N reduced.

Hence, the pixel addition is quick in frame rate, and the pixel addition having an analogue signal high in S/N is generally performed. Further, the pixel addition can perform radiographing by changing the number of pixels by the addition of a total of four pixels (hereinafter, two×two pixels addition) of two pixels in the direction to the gate wiring and two pixels in the direction to the signal wiring and a total of nine pixels of three pixels in the direction to the gate wiring and three pixels in the direction to the signal wiring.

More increased the number of pixels is, more shorter the read time becomes, and the frame rate and the S/N are improved, whereas the resolution is deteriorated since a plurality of pixels is put together into one pixel and output as one pixel (plural pixels). Hence, in view of the frame rate, S/N, and resolving power, the engineer who performs the radiographing selects the pixels according to the state of the object.

Further, the radiation imaging apparatus performs a gain correction (sensitivity correction) since there exist irregularities of the sensitivity of the conversion element such as a photoelectric conversion element and gain irregularities of Amps A1 to A4. The gain correction is performed such that an X-ray is irradiated and radiographing is performed in a state in which no object exists in advance, and the obtained image for gain correction is kept in a memory, and when an object is radiographed, the object image is divided by the image for gain correction. This image for gain correction, because of the time aging also of the conversion element, is periodically renewed by the engineer who uses the same. This renewal operation is referred to as <calibration>.

Further, since the image actually diagnosed by the doctor is an image subsequent to the gain correction performed to divide the object image by the image for gain correction, both the S/N of the object image and the S/N of the image for gain correction affect the image. Hence, when the S/N of one image is low, the S/N of the image after correction is reduced. From this, it is clear that, when the pixel addition is performed, the image for gain correction had better to use the image added with the analogue signals and having a high S/N, and in the radiation imaging apparatus having a plurality of radiographing modes different in the number of pixel additions, it is preferable that the image for gain correction is available every radiographing mode.

For example, when the object image is added with the analogue signals of 2×2 pixels and is radiographed, the image for gain correction added with the analogue signals of 2×2 pixels and radiographed is used. Further, when the object image is added with the analogue signals of 3×3 pixels and is radiographed, the image for gain correction added with the analogue signals of 3×3 pixels and radiographed is used. Further, in the case of the 2×2 pixel addition or the 3×3 pixel addition, a sum total of the number of pixels is increased by a total of four pixels or a total of nine pixels, and so when the same dosage as the X-ray not subjected to the pixel addition is irradiated, the signal output is also increased by four times or nine times, respectively. Hence, the dynamic range of the read circuit (Amp) or the AD converter ends up being saturated, and a normal signal is not output. That is, in this case, there arises a problem that acquisition of a high quality radiographed image becomes difficult.

Next, by using FIGS. 13A to 13D, an artifact caused when the object image and the image for gain correction are radiographed by different tube voltages will be described.

The radiation imaging apparatus, as shown in FIG. 13A, is configured to be laminated with phosphors on photoelectric conversion elements two-dimensionally disposed, and forms a conversion element. The phosphor converts an incident X-ray into a visible light, and converts the visible light into an electric signal by the photoelectric conversion element. The phosphor, while a material composed primarily of CsI and GOS is used, mainly uses CsI of columnar crystal excellent in DQE and MTF. This CsI is formed by a method referred to as vacuum evaporation, and generates an irregularly shaped defect as shown in FIG. 13A, which is referred to as splash. This splash is inevitably generated when CsI is vacuum-evaporated, and its complete elimination is difficult.

FIGS. 13B to 13D represent the outputs of the photoelectric conversion element of the splash defect bottom of phosphor. The splash defect portion, as compared to other normal portions, is different in film thickness of CsI, and thus different from the normal portion in the output to the tube voltage, and further, an absorbed dosage of the X-ray is different also by the tube voltage to be radiographed, thereby generating the output change of the photoelectric conversion element.

For example, as shown in FIG. 13B, when the tube voltage of the X-ray is 80 kVp, the output of the photoelectric conversion element is reduced by approximately 20% as compared to the normal portion, whereas, as shown in FIG. 13C, when the tube voltage is 60 kVp, the output of the photoelectric conversion element is reduced by approximately 10% as compared to the normal portion. Hence, for example, when the object image is radiographed by the tube voltage 60 kVp, and the image for gain correction is radiographed by the tube voltage 80 kVp, if the division of the object image by the image for gain correction is performed, the gain correction of the splash defect is unable to be performed, and this ends up emerging as a reduction of 12% as shown in FIG. 13D. Hereinafter, the gain correction performed by using the radiographed images in this manner by the different tube voltages is referred to as <different tube voltage gain correction>.

The error due to such a gain correction becomes a cause of a false diagnosis by the doctor. Such a gain corrector error happens not only to CsI, but also to phosphor of GOS, amorphous selenium that converts the X-ray directly into an electric signal without using phosphor, gallium arsenide, mercuric iodide, and the conversion element using lead iodide, thereby creating a problem in that an artifact is generated on the radiographed image.

The present invention has been carried out in view of the above described problem, and an object of the invention is to provide a radiation imaging apparatus that realizes acquisition of an object image having a high quality and no artifact when performing a gain correction for the radiographed object image.

The radiation imaging system of the present invention comprises: a radiation imaging unit for performing a radiographing of the radiation irradiated from a radiation generator for generating the radiation; a table storing unit for storing a table set with radiation conditions of the radiation of the radiation generator unit and driving conditions of the radiation imaging unit to each operation modes of the plurality of operation modes selected by a selecting unit for selecting an operation mode for performing a radiographing from among the plurality of operation modes; an image storing unit for storing an image for correction radiographed based on the conditions set with the table in a state in which no object exists to each operation modes of the plurality of operation modes; and an image processing unit for performing a gain correction processing of the radiographed object image, wherein, the image processing unit is performing the gain correction processing of the radiographed object image obtained based on the conditions set in the table of the operation mode selected by the selecting unit in a state in which the object exists using a corresponding image for correction extracted from the image storage unit based on the operation mode selected by the selecting unit. A driving method of the radiation imaging system of the present invention is a driving method of the radiation imaging system comprising: a radiation imaging unit for performing a radiographing of the radiation irradiated from a radiation generator unit for generating radiation and irradiating the same outside; and a table storage unit for storing a table set with an irradiation condition of the radiation of the radiation generator unit and a driving condition of the radiation imaging unit every each operation mode of the plurality of operation modes selected at a selecting unit for selecting an operation mode for performing the radiographing from among the plurality of operation modes; the driving method of the radiation imaging system further comprising: a storing step of storing the image for correction radiographed based on the condition set in the table in the image storage unit in a state in which no object exists every each operation mode of the plurality of operation modes; an extraction step of extracting the corresponding image for correction from the image storage unit based on the operation mode selected by the selecting unit; and an image processing step of performing the gain correction processing of the object image radiographed based on the conditions set in the table of the operation mode selected by the selecting unit in a state in which the object exists by using the image for correction extracted by the extraction step.

According to the present invention, when a gain correction is performed for the radiographed object image, an object image having a high quality and no artifact can be obtained.

Further features of the present invention will become apparent from the following description of exemplary embodiments with reference to the attached drawings.

BRIEF DESCRIPTION OF THE DRAWINGS

FIG. 3 is a view showing one example of a calibration table used for the x-ray imaging system according to the first embodiment.

FIG. 4 is a timing chart showing a driving method in a non-pixel addition of the x-ray imaging system according to the first embodiment;

FIG. 10 is a view showing one example of a calibration table used for the x-ray imaging system according to a third embodiment.

DESCRIPTION OF THE EMBODIMENTS

Hereinafter, preferable embodiments of the present invention will be described in detail with reference to the drawings. Incidentally, in various embodiments of the present invention, while the embodiment using an x-ray as a radiation will be illustrated, the present invention is not limited to this x-ray, and for example, α-ray, β-ray, γ-ray, and the like should be construed as included also in the category of the radiation.

(First Embodiment)

Figure 1:
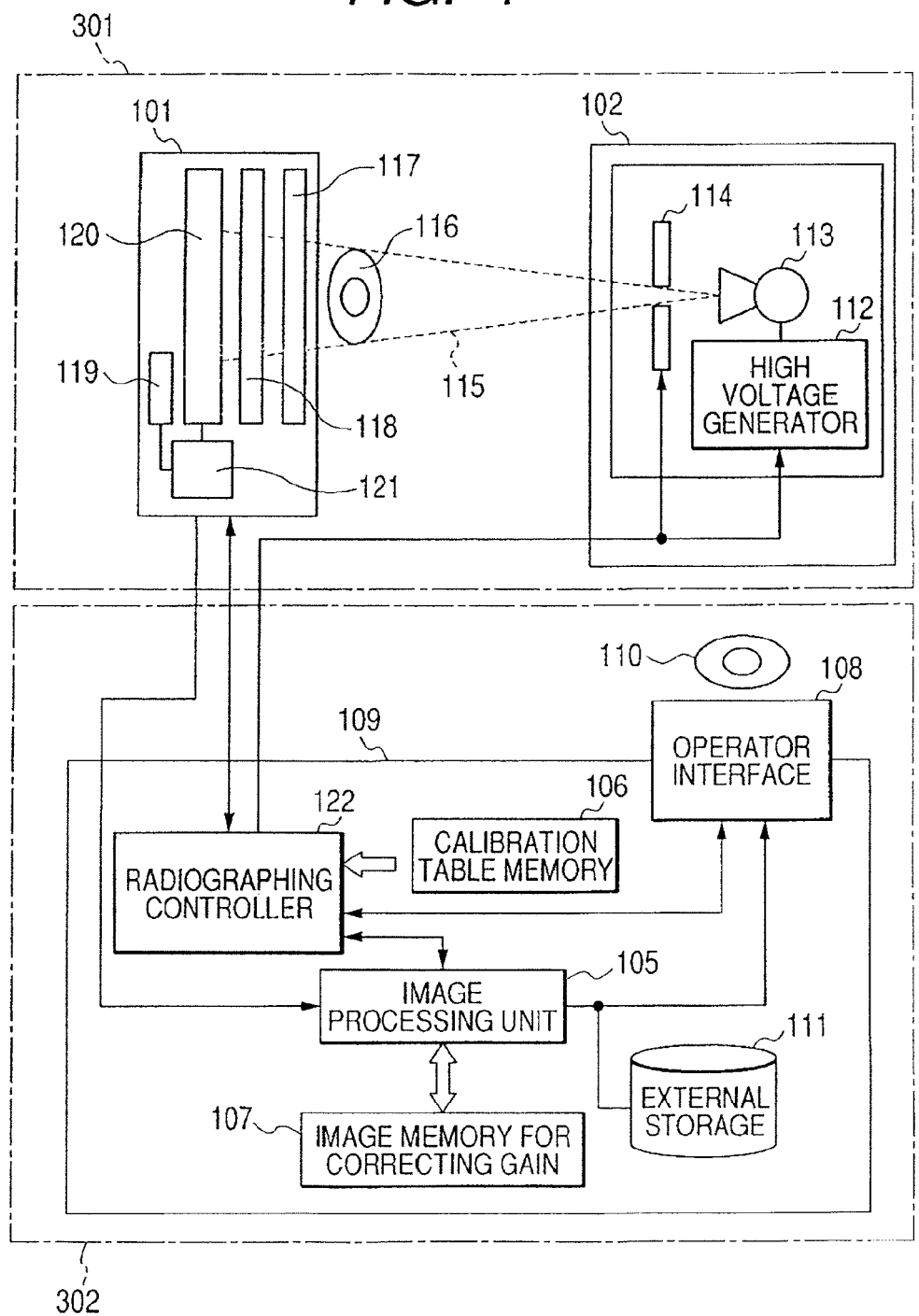
FIG. 1 is a schematic configuration view of an x-ray imaging system according to a first embodiment.

FIG. 1 is a schematic configuration view of an x-ray imaging system according to a first embodiment. As shown in FIG. 1, the radiation imaging system of the present embodiment is configured by being divided into an x-ray room 301 and an x-ray control room 302. In the x-ray room 301 are placed an x-ray imaging apparatus 101 and an x-ray generator apparatus 102. Further, a control apparatus 109 for controlling the x-ray imaging apparatus 101 and the x-ray generator apparatus 102 is placed in the x-ray control room 302, and an engineer 110 is configured to control the x-ray imaging apparatus 101 and the x-ray generator apparatus 102 from the x-ray control room 102.

The engineer 110 performs a control for the x-ray imaging apparatus 101 and the x-ray generator apparatus 102 through an operator interface 108. This operator interface 108 comprises a touch panel on a display, mouse, keyboard, joystick, foot switch, and the like. The engineer 110 can set irradiation conditions of the x-ray generator apparatus 102 such as a tube voltage, tube current, irradiation time, and pulse irradiation mode, and driving conditions of the x-ray imaging apparatus 101 such as a radiographing mode (still image mode, moving image mode, and the like) and a radiographing timing by the operator interface 108. Further, the engineer 110 can perform a setting of various pieces of information on an image processing condition, an object ID, and a processing method of the captured image by the operator interface 108. However, since nearly all pieces of the information are transferred from a radiation information system (not illustrated), there is no need to input them individually. The important operation of the engineer 110 is a confirmatory operation of the radiographed image. That is, the engineer performs judgment as to whether or not its angle is correct, an object 116 such as a patient moves, and an image processing is appropriate.

A radiographing controller 122 drives the x-ray generator apparatus 102 serving as a radiation source and the x-ray imaging apparatus 101 from the radiographing conditions based on the instruction of the engineer 110 or the radiation information system (not illustrated), and performs a control to capture image data. The radiographing controller 122 transfers the image data captured from the x-ray imaging apparatus 101 to an image processing unit 105, and after that, allows the image processing designated by the engineer 110 to be performed by the image processing unit 105, and allows this processing to be displayed on the operator interface 108. At the same time, the radiographing controller 122 allows the image processing unit 105 to perform a basic image processing such as a gain correction, offset correction, white correction, and defect correction, and stores the image data after the processing in an external storage unit 111.

Next, along with the flow of signals, the configuration and operation of the radiation imaging system of the present embodiment will be described.

The x-ray generator apparatus 102 comprises a high voltage generating source 112, x-ray tube bulb 113, and x-ray aperture 114.

The x-ray tube bulb 113 is driven by the high voltage generating source 112 controlled by the radiographing controller 122, and radiates an x-ray beam 115. The x-ray aperture 114 is driven by the radiographing controller 122, and accompanied with the change of radiographing areas, shapes the x-ray beam 115 so as not to perform unnecessary x-ray irradiation. The x-ray beam 115 is pointed at an object 116 lying down on an x-ray permeable bed for radiographing (not illustrated). This bed for radiographing is driven based on the instruction from the radiographing controller 122. The x-ray beam 115 is transmitted through the object 116 and the bed for radiographing (not illustrated), and after that, enters the x-ray imaging apparatus 101.

The x-ray imaging apparatus 101 comprises a grid 117, wavelength converter 118, x-ray exposure monitor 119, photoelectric conversion circuit unit 120, and external circuit unit 121.

The grid 117 reduces the effect of an x-ray scattering generated by the transmission of the x-ray through the object 116. This grid 117 comprises an x-ray low absorbing member and an x-ray high absorbing member, and, for example, is stripe-structured by Al and Pb. The radiographing controller 122, at the time of the x-ray irradiation, vibrates the grid 117 so that moire is not generated by the relationship of a grid ratio between the photoelectric conversion circuit unit 120 and the grid 117.

The wavelength converter 118 includes phosphor comprising one kind selected from among $Gd_2O_2S$, $Gd_2O_3$, $CaWO_4$, $CdWO_4$, CsI, and ZnS as primary material. The wavelength converter 118 has the main ingredient of its phosphor excited by incident x-ray of high energy, and outputs fluorescent radiation of the visible area by recombination energy when recombined. The fluorescent radiation is based on per se main ingredient such as $Gd_2O_3$, $Gd_2O_2S$, $CaWO_4$, and $CdWO_4$, or based on the fluoresce center substance activated inside the main ingredient such as CsI:Ti and ZnS:Ag. Adjacent to this wavelength converter 118, the conversion circuit unit 120 is disposed.

The conversion circuit unit 120 subjects a radiation to wavelength-conversion to light by the wavelength converter 118, and converts a photon of the light subjected to the wavelength conversion into an electric signal. That is, the conversion circuit unit 120 radiographs the radiation image of the object 116. Further, in the conversion circuit unit 120 is disposed each pixel (unit pixel) including the photoelectric conversion element (radiographing element) in a two-dimensional procession (two-dimensional matrix). In each pixel, a conversion element for converting the radiation into a charge includes the wavelength converter 118 and the photoelectric conversion element.

The x-ray exposure monitor 119 is for monitoring the amount of an x-ray transmission. The x-ray exposure monitor 119 may directly detect the x-ray by using a light receiving element of crystal silicon and the like or may detect a light from the wavelength converter 118. In the present embodiment, a visible light (light in proportion to the x-ray dosage) transmitted through the conversion circuit unit 120 is detected by an amorphous silicon light receiving element of the x-ray exposure monitor 119 which is deposited on a rear surface of the substrate having the conversion circuit unit 120 formed thereon, and this information is transmitted to the radiographing controller 122. The radiographing controller 122, based on the information from the x-ray exposure monitor 119, drives the high voltage generating source 112 so as to shut off or adjust the x-ray.

The external circuit unit 121 comprises a driving circuit unit for driving the conversion circuit unit 120, a readout circuit unit for reading a signal from each pixel of the photoelectric conversion circuit unit 120, and a power source circuit unit. This external circuit unit 145 drives the conversion circuit unit 120 under a control of the radiographing controller 122, and reads the signal from each pixel, and outputs it to the control apparatus 109 of the x-ray control room 302 as an image signal (image data).

The control apparatus 109 comprises the image processing unit 105, calibration table memory 106, image memory for gain correction 107, operator interface 108, external storage unit 111, and radiographing controller 122.

The image signal output from the x-ray imaging apparatus 101 is transferred from the x-ray room 301 to the image processing unit 105 in the x-ray control room 302. At this transfer time, since the noise accompanied with the x-ray generation is loud inside the x-ray room 301, there is a possibility that the image signal (image data) is sometimes not accurately transferred because of the noise. Hence, the increase of noise resistance of the transfer route is required. For example, the transfer route is preferably provided with an error correction function or otherwise uses a pair twisting wire with shield or an optical fiber by differential driver.

The image processing unit 105, based on the instruction from the radiographing controller 122, switches over the display data. Further, the image processing unit 105 performs various types of correction processing such as an offset correction, gain correction and defect correction for the image data, and also a space filtering processing, recursive processing, and the like in real time. Further, the image processing unit 105 performs a gradation processing, scattered radiation correction processing, spatial frequency processings of various types, and the like as occasion demands. Incidentally, in the present embodiment, while the image processing unit 105 is provided outside of the x-ray imaging apparatus 101, it may be provided inside the radiation imaging apparatus 101.

The image data processed by the image processing unit 105 is displayed on the operator interface 108 as an image. Further, at the same time with the real time image processing, the basic image data subjected to the image data correction processing only is stored in an external storage unit 111. This external storage unit 111 is preferably a data storage unit which is high-volume and high speed and satisfies high reliability, and for example, a hard disc array such as RAID is preferable. Further, based on the instruction from the operator (engineer 110), the image data stored in the external storage unit 111 is stored in another external storage unit. At this time, the image data is re-configured so as to satisfy the predetermined standard (for example, IS&C), and after that, it is stored in another external storage unit. Other external storage units, for example, include a magnetic optical disc and a hard disc inside a file server on LAN and the like.

In the calibration table memory 106 is stored a calibration table provided with the driving condition of the x-ray imaging apparatus 101 in each operation mode of the x-ray imaging system and the irradiation conditions of the x-ray of the x-ray generator apparatus 102. In the image memory for gain correction 107 is stored each image data for gain correction radiographed in a state in which the object 116 does not exist for each operation mode of the x-ray imaging system. Incidentally, in the present embodiment, while the calibration table memory 106 and the image memory for gain correction 107 are provided outside of the x-ray imaging apparatus 101, they may be provided inside the radiation imaging apparatus 101.

The x-ray imaging system of the present embodiment can be also connected to the LAN through a LAN board, and is configured to have data compatibility with HIS. This LAN is connected with a monitor for displaying still images or moving images, file server for filing the image data, image printer for outputting the image on a film, image processing terminal for performing complex image processing and diagnostic support, and the like. Incidentally, it goes without saying that this LAN is connected with a plurality of x-ray imaging systems. Further, the x-ray imaging system in the present embodiment outputs the image data according to the predetermined protocol (for example, DICOM). In addition, by using a monitor which is connected to the LAN, a real time remote diagnosis by the doctor can be performed at the x-ray imaging time.

Figures 2, 2A:
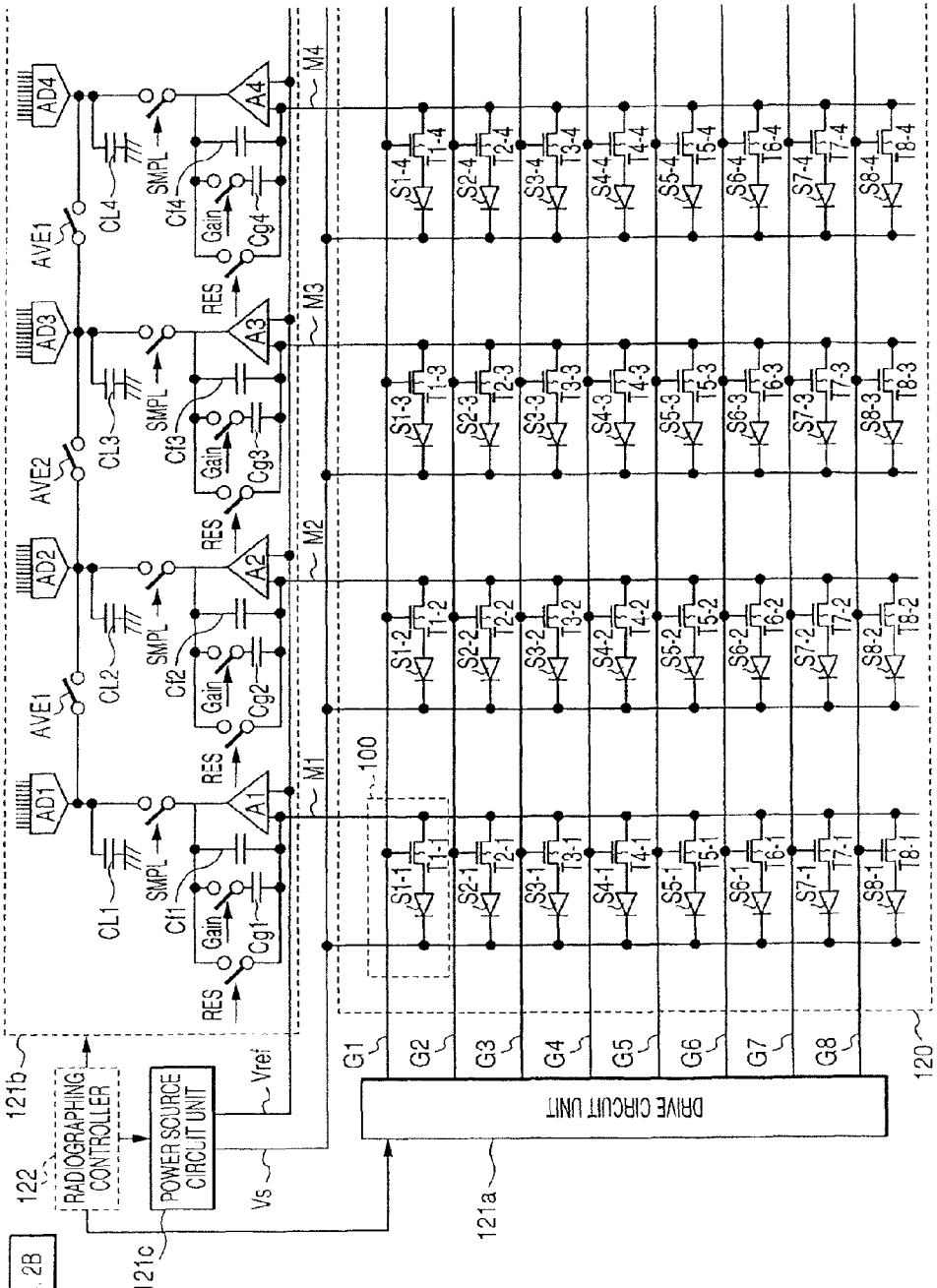
FIG. 2 which is composed of FIGS. 2A and 2B are equivalent circuit diagrams showing a detailed configuration in an x-ray imaging apparatus of the x-ray imaging system according to the first embodiment.
Figure 2B:
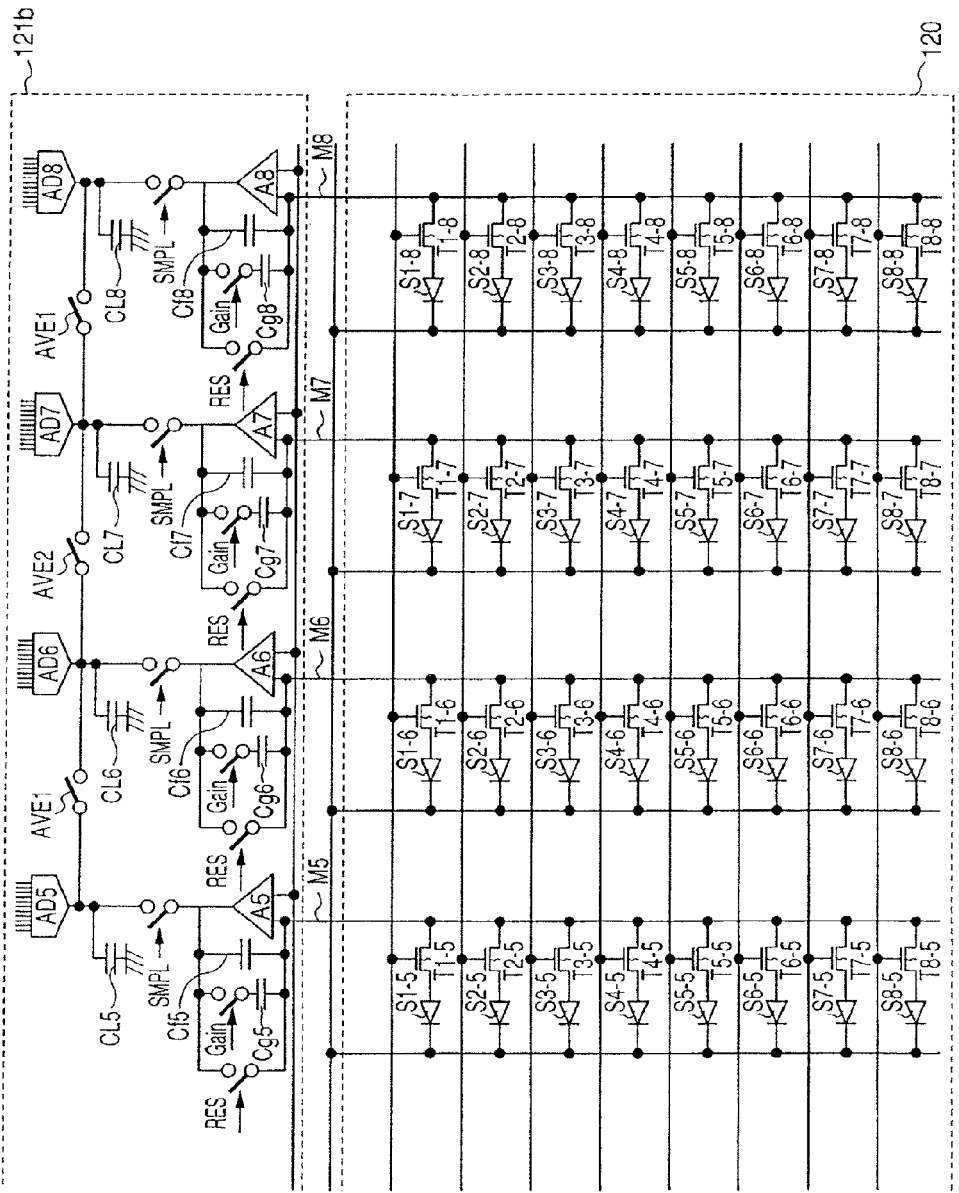

Next, the x-ray imaging apparatus 101 will be described in detail. FIGS. 2A and 2B are equal circuit diagrams showing a detailed configuration in the x-ray imaging apparatus 101 of the x-ray imaging system according to the first embodiment. Here, in FIGS. 2A and 2B, from among each component part comprising the radiation imaging apparatus 101, the conversion circuit unit 120, driving circuit unit 121a provided in the external circuit unit 121, readout circuit unit 121b, and power source circuit unit 121c are shown. The conversion circuit unit 120, driving circuit unit 121a, readout circuit unit 121b, and power source circuit unit 121c shown in these FIGS. 2A and 2B are, for example, composed by using amorphous silicon thin film semiconductor.

This x-ray imaging apparatus 101, based on a control from the radiographing controller 122, is configured to be able to be driven in operation modes of various types including a moving image radiographing mode and a still image radiographing mode.

In the conversion circuit unit 120 of FIGS. 2A and 2B are disposed pixels (unit pixels) 100 in a two-dimensional matrix pattern, which comprise one piece each of photoelectric conversion elements S1-1 to S8-8 comprising the conversion elements for converting the radiation into the electric signals (electric charges) and switch elements T1-1 to T8-8 for capturing (transferring) electric signals from the photoelectric conversion elements. In FIGS. 2A and 2B, for convenience, a total of 64 pieces of the unit pixels of eight pixels×eight pixels is shown.

Each unit pixel 100 of this conversion circuit unit 120, for example, is formed by using amorphous silicon thin film semiconductor on an insulating substrate such as glass. Further, the photoelectric conversion elements S1-1 to S8-8 are formed by a MIS type structure or a PIN type structure with amorphous silicon taken as primary material. In this case, on the photoelectric conversion elements S1-1 to S8-8, wavelength converters 118 for converting the radiation into a light of the detectable wavelength area by the photoelectric conversion elements are provided, and the photoelectric conversion elements are incident with a visible light from the wavelength converters 118. Incidentally, the photoelectrical conversion elements S1-1 to S8-8 may absorb incident radiation (x-ray) and directly convert it into the electric charge. The photoelectric conversion element of the direct type, for example, takes one kind selected from amorphous selenium, gallium arsenide, mercuric iodide, lead iodide, and cadmium telluride as primary material. Further, as the switch elements T1-1 to T8-8, a TFT (Thin Film Transistor) formed by amorphous silicon on the insulating substrate such as glass can be suitably used.

The photoelectric conversion elements S1-1 to S8-8, for example, comprise photo diodes, which are reverse-biased. That is, a cathode electrode side of the photo diode is biased to + (plus). A bias wiring Vs is a common wiring for supplying a bias (Vs) to each photo diode, and is connected to the power source circuit unit 121c.

The gate wirings G1 to G8 connect the switch element of each pixel in a row direction, and are the wirings for turning ON and OFF each of the switch elements T1-1 to T8-8. The driving circuit unit 121a supplies a driving signal (pulse) to each of the gate wirings G1 to G8 so as to drive each of the switch elements T1-1 to T8-8 and drive each of the photoelectric conversion elements S1-1 to S8-8. The signal wirings M1 to M8 are wirings for connecting the switch element of each pixel in a column direction and reading the electric signals (electric charges) of the photoelectric conversion elements S1-1 to S8-8 through the switch elements T1-1 to T8-8 to the readout circuit unit 121b.

A switch RES is for resetting capacitors Cf1 to Cf8. A switch Gain is a gain selector switch of Amp of the readout circuit unit 121b. The Amps A1 to A8 are for amplifying the electric signals from the signal wirings M1 to M8. A Vref wiring is a wiring for supplying a reference power source from the power source circuit unit 121c to the Amps A1 to A8. Capacitors CL1 to CL 8 are sample-hold capacitors for temporarily storing the electric signals amplified by the Amps A1 to A8. A switch SMPL is for performing a sample hold. Switches AVE1 and AVE2 are switches for subjecting the electric signals sample-held to a pixel addition (averaging out). AD converters ADC1 to ADC8 are for converting the electric signals (analogue signals) sample-held by the sample-hold capacitors CL1 to CL8 into digital signals. The digital signals after this AD conversion, for example, are output to the image processing unit 105 and the like, and are subjected to the predetermined processing such as the image processing, and after that, the display and storage of the processed image data are performed.

Next, information stored in the calibration table memory 106 will be described. FIG. 3 is a view showing one example of a calibration table used for the x-ray imaging system according the first embodiment. The calibration table shown in FIG. 3 is stored in the calibration table memory 106. Here, the calibration table means a table for setting radiographing conditions to the x-ray imaging apparatus 101 and the x-ray generator apparatus 102 when performing a calibration. Specifically, the calibration table memory 106 is specified in the irradiation conditions (irradiation mode, tube voltage, tube current, and irradiation time) in the x-ray generator apparatus 102 and the driving conditions (gain and driving method) in the x-ray imaging apparatus 101 according to each operation mode. Here, the <gain> indicates an amplification factor of the Amps A1 to A8 of the readout circuit unit 121b. Further, the <driving method> relates to the number of additions when reading the electric signal of the unit pixel 100.

Further, in the present embodiment, as the driving conditions in the x-ray imaging apparatus 101, in addition to the gain and driving method shown in FIG. 3, a mode in which the calibration table is formed by including the voltage applied to the photoelectric conversion element and the voltage applied to the switch element can be also applied.

Here, the operation modes in the x-ray imaging system of the present embodiment will be described.

In a still image radiographing mode, since only one sheet of image is radiographed, there is no need to quicken a frame rate, and a resolving power is required, and therefore, the addition driving of the unit pixel is not performed. Further, as shown in FIG. 3, a moving image photographing mode includes a total of three types, and each is different in the number of additions of the unit pixel. Specifically, the moving image radiographing mode includes three modes of a first moving radiographing mode (one×one pixel addition: non-pixel addition), a second moving image radiographing mode (2×2 pixel addition), and a third moving image radiographing mode (4×4 pixel addition).

In the addition processing of the unit pixel, since the signals of a plurality of unit pixels are read simultaneously, the frame rate becomes fast and the S/N becomes also high, but because the plurality of unit pixels are put into one pixel and output, the resolving power is reduced. Hence, to which item from among the frame rate, S/N, and resolving power, the engineer 110 gives priority to radiograph depending on the condition and the like of the object 116 is selected by using the operator interface 108. In the calibration table of the present embodiment, three tube voltage modes of low tube voltage/medium tube voltage/high tube voltage are specified every four radiographing modes shown in FIG. 3. The image processing unit 105 extracts an image for gain correction in the tube voltage closest to a tube voltage having actually radiographed the object 116 from the image memory for gain correction 107, and performs a gain correction of the object image by using the extracted image for gain correction.

Next, by using the timing chart shown in FIGS. 4 to 6, the operation of the x-ray imaging system according to the present embodiment will be described.

FIG. 4 is a timing chart showing a driving method in the non-pixel addition of the x-ray imaging system according to the first embodiment. Based on this timing chart, the operations of the conversion circuit unit 120, driving circuit unit 121a and readout circuit unit 121b as shown in FIGS. 2A and 2B will be described.

First, the operation in a photoelectric conversion period (x-ray irradiation period) will be described.

In a state in which all the switch elements are turned off, when the x-ray is irradiated pulse-wise from the x-ray generator apparatus 102, an x-ray or a light converted in wavelength from the x-ray is irradiated to each photoelectric conversion element. Electric signals (electric charges) according to the quantity of the x-ray or light are accumulated in each photoelectric conversion element.

At this time, when the above described wavelength converter 118 for converting the x-ray into a visible light is used, a member for guiding the visible light corresponding to the amount of the x-ray to the photoelectric conversion element side is used, or alternatively, the wavelength converter 118 may be disposed extremely close to the photoelectric conversion element. Incidentally, even after the x-ray becomes non-irradiative, each photoelectric conversion element holds the photoelectrically converted electric signal (electric charge).

Next, the operation during the readout period will be described. The readout operation is performed in order of the photoelectric conversion elements S1-1 to S1-8 of the first line, the photoelectric conversion elements S2-1 to S2-8 of the second line, and the photoelectric conversion elements S3-1 to S3-8 of the third line, and this readout is performed up to the photoelectric conversion elements S8-1 to S8-8 of the eighth line.

First, to read out the electric signals (electric charges) accumulated in the photoelectric conversion elements S1-1 to S1-8 of the first line, the gate wiring G1 connected to the switch elements T1-1 to T1-8 of the first line from the driving circuit unit 121a is given a driving signal (pulse). At this time, the driving circuit unit 121a, based on a control from the radiographing controller 122, outputs the driving signal to the gate wiring G1. As a result, the switch elements T1-1 to T1-8 of the first line are put into a turned on state, and the electric signals based on the electric charges accumulated in the photoelectric conversion elements S1-1 to S1-8 of the first line are transferred through the signal wirings M1 to M8.

The electric signals transferred to the signal wirings M1 to M8 are amplified by the Amps A1 to A8 according to capacitance of the capacitors Cf1 to Cf8. The amplified electric signals are sample-held in the capacitors CL-1 to CL8 by SMPL signals based on a control from the radiographing controller 122. After that, the electric signals sample-held by the capacitors CL1 to CL8 are AD-converted by the AD converters AD1 to AD8, and are output to the image processing unit 105 and the like as digital data.

Similarly to the readout operation of the photoelectric conversion elements S1-1 to S1-8 of the first line, the readout operation of the photoelectric conversion elements S2-1 to S2-8 of the second line and the readout operation of the photoelectric conversion elements S3-1 to S3-8 of the third line are performed in order, and subsequently, the readout operations up to the fourth line to the eighth line are performed.

In this manner, the x-ray is converted into the visible light by using the wavelength converter 118, and the visible light is converted into the electric charge by each photoelectric conversion element, and the x-ray information is readout as the electric signal, so that the information on the object 116 can be obtained.

Next, by using FIG. 5, the driving method of the 2×2 pixel addition will be described.

Figure 5:
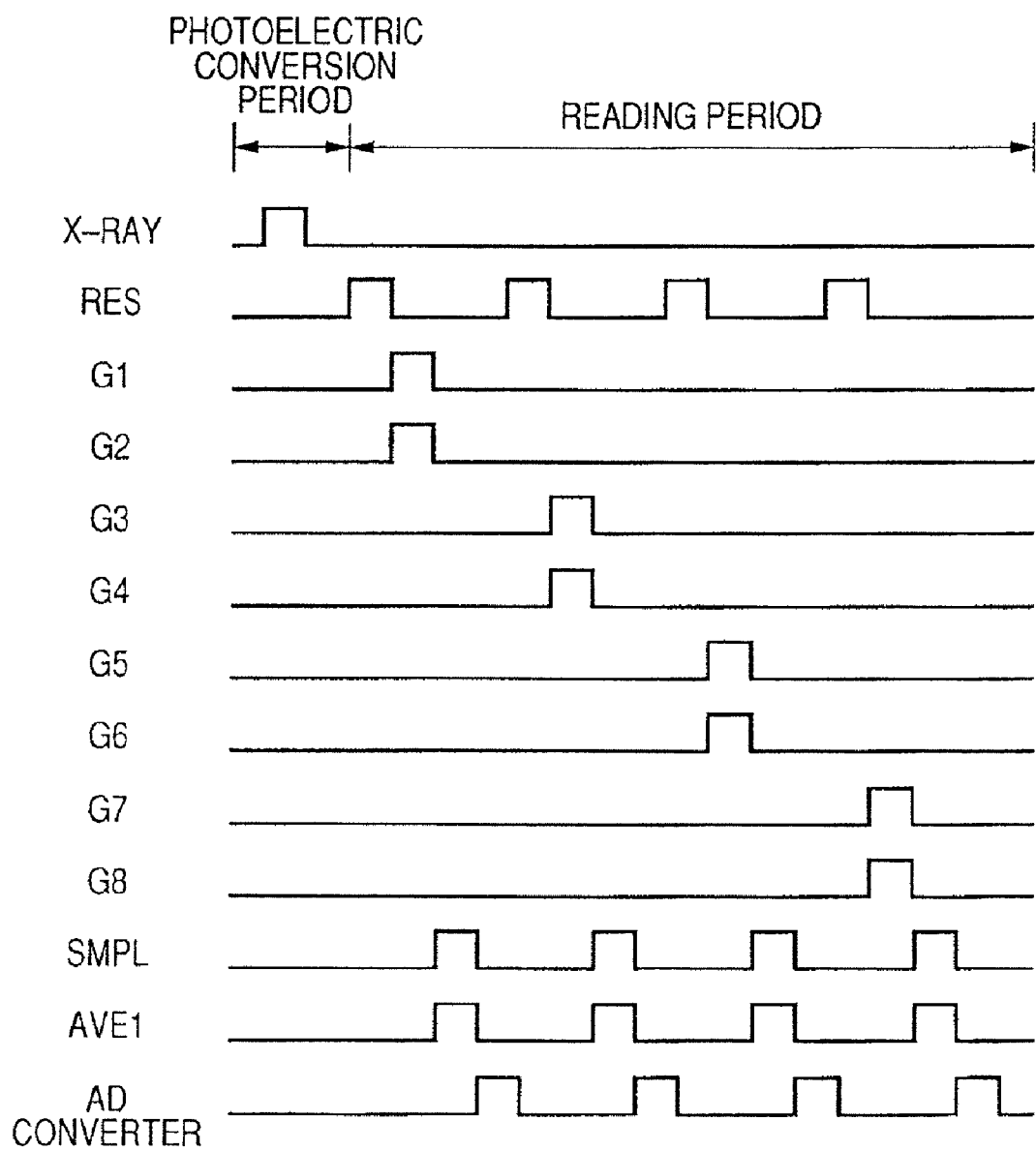
FIG. 5 is a timing chart showing a driving method in a 2×2 pixel addition of the x-ray imaging system according to the first embodiment.

FIG. 5 is a timing chart showing the driving method in the 2×2 pixel addition of the x-ray imaging system according to the first embodiment.

The driving in the 2×2 pixel addition, as compared to the case where the pixel addition shown in FIG. 4 is not performed, is different in the number of gate wirings for turning ON/OFF simultaneously. As shown in FIG. 4, in the driving of the non-pixel addition, while the gate wirings are turned ON/OFF in order of G1, G2, G3 . . . , in the driving of the 2×2 pixel addition, each group of G1 and G2, G3 and G4, G5 and G6, and G7 and G8 is turned ON/OFF simultaneously.

When the gate wirings G1 and G2 are simultaneously turned ON by performing the driving of such 2×2 pixel addition, the switch elements T1-1 to T2-8 are simultaneously opened, and for example, a sum of the electric signals (electric signals two times the non-pixel addition) of the photoelectric conversion elements S1-1 and S2-1 is accumulated in the capacitor Cf1. Further, in the driving of the 2×2 pixel addition, since the readout time becomes 1/2 as compared to the case where the pixel addition is not performed, the frame rate becomes twofold.

Further, in the driving of the 2×2 pixel addition, the pixel addition is performed also in the direction to the signal wiring. Specifically, by the input of the AVE1 signal based on a control from the radiographing controller 122 after being sample-held in the capacitors CL1 to CL8, each capacitance of the capacitors CL1 and CL2, CL3 and CL4, CL5 and CL6, and CL7 and CL8 are combined, and the sample-held signals are averaged out. As a result, the electric signals of the 2×2 pixels are added into one pixel, and are output as a plural pixel. In this case, while the size of the electric signal does not change, the noise becomes $1/(\sqrt{2})$ times, so that the S/N becomes $(\sqrt{2})$ times.

Next, by using FIG. 6, the driving method of the 4×4 pixel addition will be described.

Figure 6:
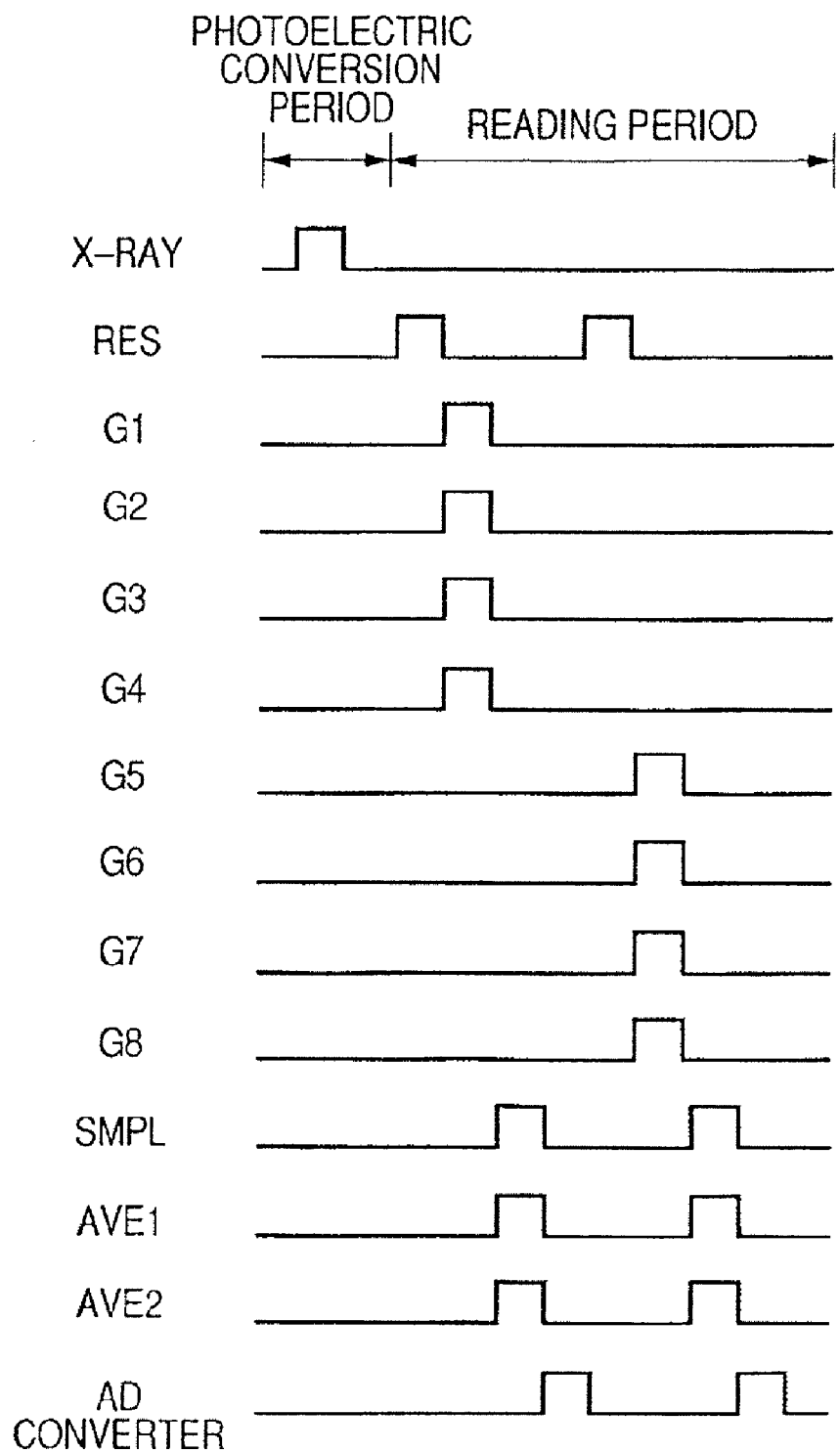
FIG. 6 is a timing chart showing the driving method in a 4×4 pixel addition of the x-ray imaging system according to the first embodiment.

FIG. 6 is a timing chart showing a driving method in the 4×4 pixel addition in the x-ray imaging system according to the first embodiment.

In the driving in the 2×2 pixel addition, while the gate wirings are turned ON/OFF two pieces simultaneously, in the driving in the 4×4 pixel addition, the gate wirings are turned ON/OFF four pieces simultaneously so as to perform the readout. Hence, fourfold signal is output. Further, as compared to the driving in the 2×2 pixel addition, the readout period is also shortened by 1/4, and the frame rate becomes fourfold.

With respect to the pixel addition in the direction to the signal wiring, by the pulse input of the AVE1 signal and the AVE2 signal based on a control from the radiographing controller 122 after being sample-held in the capacitors CL1 to CL8, each capacitance of the capacitors CL1-CL4 and the capacitors CL5 to CL8 is combined. As a result, the electric signals sample-held in each of the capacitors CL1 to CL8 are averaged out, and the averaged analogue signals are AD-converted, and the electrical signals of the 4×4 pixels are added into one pixel, and are output as a plural pixel.

As described above, by the driving of the non-pixel addition, 2×2 pixel addition, and 4×4 pixel addition, the S/N can be made high and the frame rate can be made fast.

Next, the radiographing of the image for gain correction, which is the characteristic of the present invention, will be described.

In the present embodiment, to obtain the radiographed image having high S/N and no artifact, the image for gain correction is radiographed every radiographing mode. In the present embodiment, as shown in FIG. 3, a total of four operation modes of one still image radiographing mode and three moving image radiographing modes are set. In the present embodiment, as shown in FIG. 3, the images for gain correction in three tube voltages different in the low tube voltage, medium tube voltage, and high tube voltage every operation mode are radiographed. Hence, in the present embodiment, the images for gain correction of 12 sheets=four radiographing modes×three tube voltages are radiographed.

Further, even when the same x-ray is irradiated, the signal amount output from the photoelectric conversion circuit unit 120 is different every radiographing mode. For example, in the driving in the 2×2 pixel addition which is a second moving image radiographing mode, the addition processing in the direction to the gate wiring is performed, whereas, in the direction to signal wiring, because of the averaging out, the signals two times that of the non-pixel addition mode are output. Hence, when the same x-ray amount as the first moving image radiographing mode (one×one pixel addition) is irradiated at the time of the second moving image radiographing mode (2×2 pixel addition), dynamic ranges of the Amps and AD converters of the readout circuit unit 121b sometimes end up saturating.

Further, in the moving image radiographing mode and the still image radiographing mode, the gains of the Amps A1 to A8 of the readout circuit unit 121b are different. The switching over of the gains at this time is performed such that, by the input of the gain signals based on a control of the radiographing controller 122, the switch Gains shown in FIGS. 2A and 2B are operated, thereby switching over the integral capacities (Cg and Cf) of the Amps A1 to A8 of the readout circuit unit 121b.

Since the output of each of the Amps A1 to A8 of the readout circuit unit 121b is the output=1/integral capacity, smaller the integral capacity is, higher the gain becomes, and higher level the output signal is. In the still image radiographing, since one sheet only of image is radiographed, no problem is caused even if the x-ray amount to be irradiated is slightly larger, whereas, in the case of the moving image radiographing, the time to irradiate the x-ray is long, and therefore, the x-ray amount to be irradiated per one image sheet is required to be limited to the minimum. Hence, to obtain the electric signals from the least x-ray amount, readout of the high again is performed.

In this manner, the moving image radiographing mode and the still image radiographing mode, the number of additions of the unit pixel, and the electric signals output from the photoelectric conversion circuit 120 by the tube voltage and the like of the x-ray tube bulb 113 are different. Hence, in consideration of the dynamic range of each of the Amps A1 to A8 and AD converters AD1 to AD8 of the readout circuit unit 121b, the conditions of the x-ray radiographing are required to be decided. However, to radiograph the image for gain correction, it is difficult for the engineer 110 to decide its condition one by one every operation mode and perform the setting.

Hence, in the present embodiment, the calibration table set with the irradiation conditions of the x-ray and the driving conditions of the x-ray imaging apparatus per each operation mode is stored in the calibration table memory 106 in advance. Based on the data of this calibration table, the radiographing controller 122 allows the x-ray imaging apparatus 101 and the x-ray generator apparatus 102 to operate, and therefore, the engineer 110 can perform the calibration only by depressing an exposure button (not shown) every operation mode. Here, in the present embodiment, for example, the operator interface 108 comprises the exposure button (not shown).

Next, the acquisition processing of the image for gain correction will be described.

Figure 7:
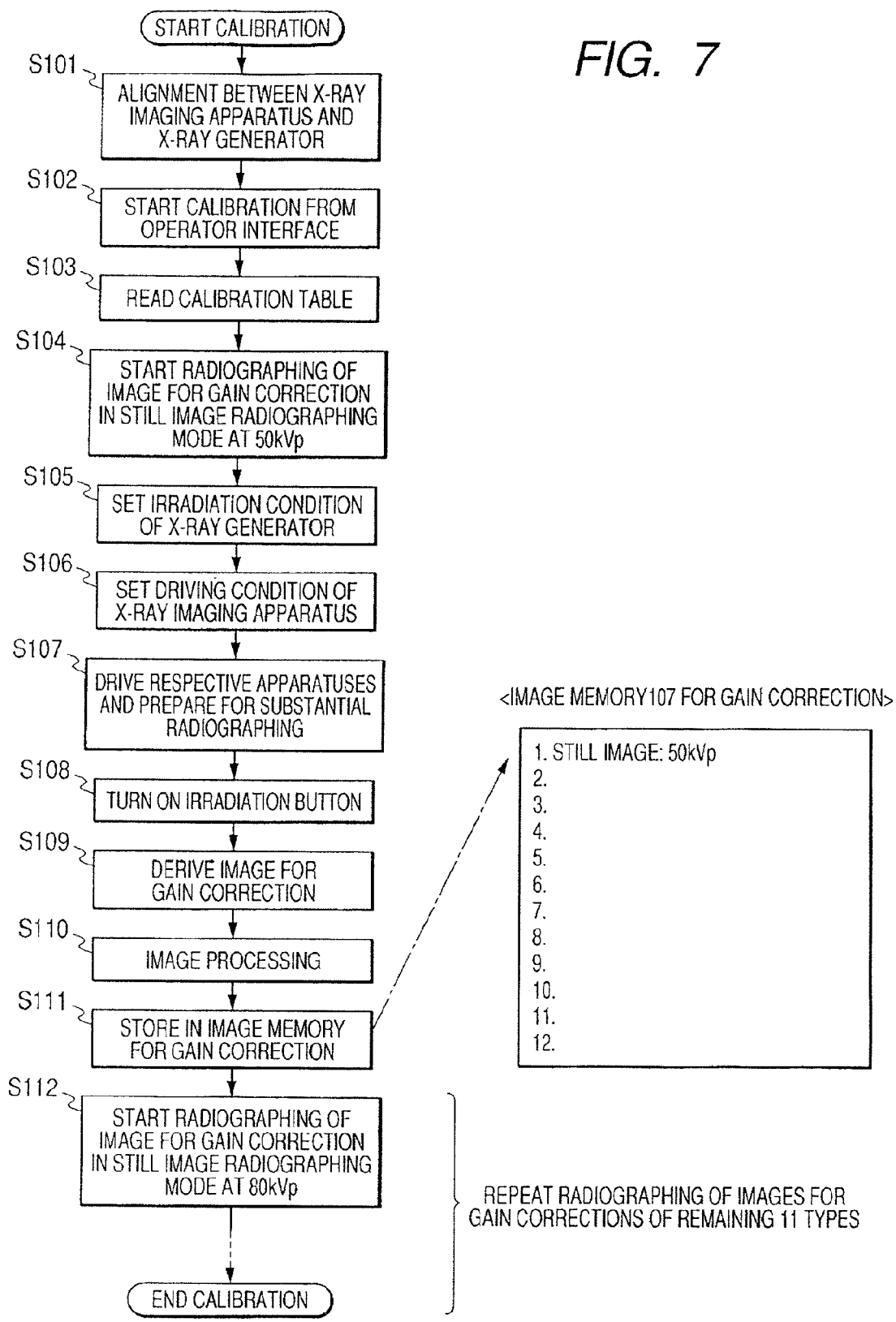
FIG. 7 is a flowchart showing an acquisition processing of an image for gain correction of the x-ray imaging system according to the first embodiment.

FIG. 7 is a flowchart showing the acquisition processing of the image for gain correction of the x-ray imaging system according to the first embodiment. That is, FIG. 7 is a flowchart showing a procedure in the calibration.

First, when starting the calibration, the engineer 110 operates the operator interface 108, and performs an alignment between the x-ray imaging apparatus 101 and the x-ray generator apparatus 102 (step S101). Specifically, the engineer 110 performs the alignment in such a manner that an irradiation center of the x-ray by the x-ray tube bulb 113 is positioned at the center of the x-ray imaging apparatus 101. Subsequently, the engineer 110 instructs the start of the calibration from the operator interface 108 (step S102).

The radiographing controller 122 having received the start of the calibration from the operator interface 108 reads the calibration table stored in the calibration table memory 106 (step S103). In the present embodiment, though a mode of storing the calibration table in a dedicated memory 106 is shown, for example, the mode may be such that the table is stored in the external storage unit 111 with no dedicated memory 106 provided.

Subsequently, the radiographing controller 122, according to the order of the calibration table, first performs a processing to start the radiographing of the image for gain correction in the case where the x-ray tube bulb 113 is at the low tube voltage (50 kVp) in the still image radiographing mode shown in FIG. 3 (step S104). Here, when radiographing the image for gain correction, the radiographing is performed in a state in which no object 116 exists.

Subsequently, the radiographing controller 122 performs the setting of the irradiation conditions (irradiation mode, tube voltage, tube current and irradiation time) of the x-ray shown in the calibration table of FIG. 3 for the x-ray generator apparatus 102 (step S105). Specifically, at step S105, the irradiation conditions are set for the x-ray generator apparatus 102 to the effect that the irradiation mode is <general>, the tube voltage of the x-ray tube bulb 113 is <50 (kVp)>, the tube current is <125 (mA)>, and the irradiation time is <50 (ms)>.

As described above, in the present embodiment, as the setting of the irradiation conditions of the x-ray for the x-ray generator apparatus 102, the tube voltage of the x-ray tube bulb 113, tube current, irradiation time and irradiation mode of the x-ray are set. Further, other than these conditions, as the setting of the irradiation conditions of the x-ray for the x-ray generator apparatus 102, an x-ray aperture 114 can be also worked together.

Subsequently, the radiographing controller 122 performs the setting of the driving conditions (gain and driving method) shown in the calibration table of FIG. 3 for the x-ray radiographing apparatus 101 (step S106). Specifically, at step S106, the driving conditions are set for the x-ray imaging apparatus 101 to the effect that the gain is <1> and the driving method is the <still image driving>.

As described above, in the present embodiment, as the setting of the driving conditions for the x-ray imaging apparatus 101, the driving method (driving timing) and the gain are set. The setting conditions of the x-ray imaging apparatus 101 and the x-ray generator apparatus 102 stored in the calibration table are decided when the x-ray imaging apparatus 101 or the x-ray generator apparatus 102 is installed in the hospital, and after installing, the calibration is periodically performed according to the calibration table.

Subsequently, the radiographing controller 122 sets the radiographing conditions in the x-ray imaging apparatus 101 and the x-ray generator apparatus 102, and after that, drives the x-ray imaging apparatus 101 and the x-ray generator apparatus 102 so as to prepare for radiographing (step S107), and waits for the depression of the exposure button (not shown) by the engineer 110.

When the exposure button (not illustrated) is depressed by the engineer 110 and the exposure button is turned on, the radiographing controller 122 detects this (step S108).

Subsequently, the radiographing controller 122, based on the radiographing conditions set at step S105 and S106, allows the x-ray imaging apparatus 101 and the x-ray generator apparatus 102 to be driven, and performs the capturing of the radiographed image (step S109). Specifically, under the irradiation conditions set at step S105, the x-ray is irradiated from the x-ray generator apparatus 102 to the x-ray imaging apparatus 101. In the x-ray imaging apparatus 101, the x-ray from the x-ray generator apparatus 102 is received by the photoelectric conversion circuit unit 120, and based on the driving conditions set at step S106, the image data radiographed by the driving circuit unit 121a and the readout circuit unit 121b is read by the control apparatus 109. This image data read by the control apparatus 109 is the image data for gain correction used for the gain correction processing.

Subsequently, the image processing unit 105, based on a control from the radiographing controller 122, performs a basic processing such as an offset correction for the image data for gain correction read from the x-ray imaging apparatus 101 (step S110). Next, the image processing unit 105, based on a control from the radiographing controller 122, holds the image data for gain correction which is subjected to the image processing in the image memory 107 for gain correction (step S111).

By going through the processings of these steps S104 to S111, the acquisition processing of the image for gain correction is performed in the case where the x-ray tube bulb 113 is at the low tube voltage (50 kVp).

Subsequently, the radiographing controller 122, by the still image radiographing mode shown in FIG. 3 according to the order of the calibration table, performs a processing of starting the radiographing of the image for gain correction in the case where the x-ray tube bulb 113 is at the medium tube voltage (80 kVp) (step S112). From then onward, the radiographing controller 122 repeats the same processing as the acquisition processing (steps S104 to s111) of the image for gain correction according to the order of the calibration table of FIG. 3 in the case where the x-ray tube bulb 113 is at the low tube voltage, so that the images for gain correction of the remaining eleven types shown in FIG. 3 can be obtained. As a result, the image data for gain correction every operation mode of a total twelve types shown in FIG. 3 can be stored in the image memory 107 for gain correction.

In the first embodiment, though the image for gain correction is radiographed one sheet every operation mode, the images of n sheets are radiographed every operation mode, and the images of the n sheets subjected to an averaging-out processing can be also applied as the images for gain correction. In this manner, the images subjected to an averaging-out processing are taken as the images for gain correction, so that the correction images having a noise reduced to $1/(\sqrt{n})$ and high in S/N can be obtained.

In this manner, when the acquisition processing of the image for gain correction shown in FIG. 7 is performed, the engineer 110 only performs the operations of (1) alignment between the x-ray imaging apparatus 101 and the x-ray generator apparatus 102 (step S101), (2) issuance of the instruction to start the calibration from the operator interface 108 (step S102), and (3) depression of an irradiation button (not illustrated) every operation mode (12 times) (step S108), and since there is no need to perform the setting of radiographing conditions for the x-ray imaging apparatus 101 and the x-ray generator apparatus 102 every operation mode, no error in the calibration arises, and moreover, the number of man-hours can be suppressed to the minimum.

Next, the actual object radiographing operation in the case where the object 116 is disposed will be described.

Figure 8:
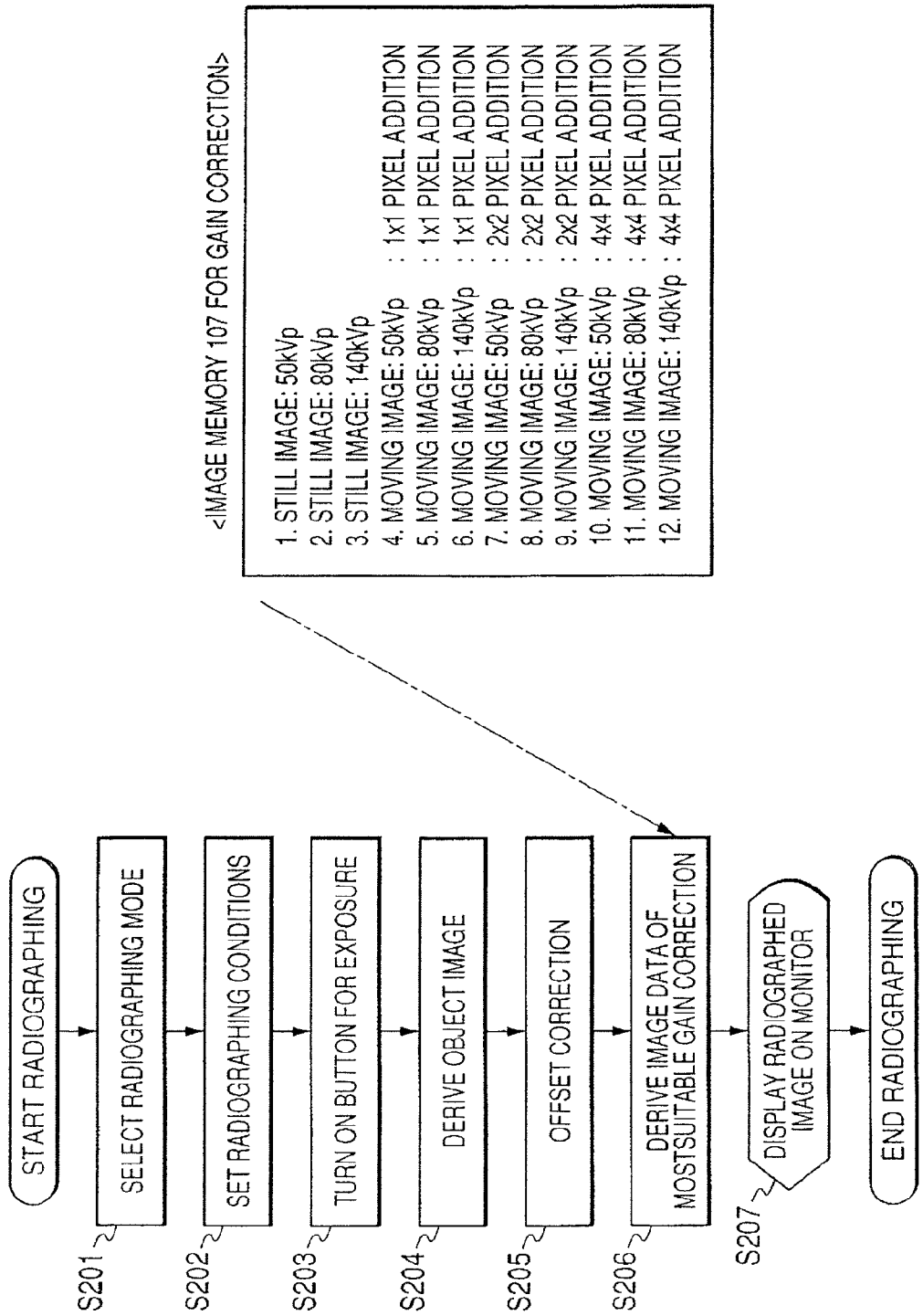
FIG. 8 is a flowchart showing the processing in the radiographing operation of the x-ray imaging system according to the first embodiment.

FIG. 8 is a flowchart showing the processing in the radiographing operation of the x-ray imaging system according to the first embodiment.

Before starting the object radiographing, the engineer 110 allows the object 116 to stand up or lie down at the predetermined position between the x-ray imaging apparatus 101 and the x-ray generator apparatus 102, and performs confirmation of the positional relationship between the object 116 and the x-ray imaging apparatus 101 and confirmation of the angle of the object 116.

Subsequently, the engineer 110 selects an operation mode (radiographing mode) to perform the object radiographing from among a total of 12 types of operation modes shown in FIG. 3 having performed the calibration by operating the operator interface 108 (step S201). At this time, for example, a mode may be adapted such the region to be radiographed and the operation mode are kept associated, and the engineer 110 selects the region to be radiographed, so that the radiographing mode is selected.

Subsequently, the radiographing controller 122, based on the operation mode selected at step S201, refers to the calibration table, and sets the radiographing conditions in the x-ray imaging apparatus 101 and the x-ray generator apparatus 102 (step S202). Here, for example, at step S201, consider the case where the operation mode in which the x-ray tube bulb 113 is at the <low tube voltage> in the <still image radiographing mode> is selected. In this case, the radiographing controller 122 sets the irradiation conditions for the x-ray generator apparatus 102 to the effect that the irradiation mode is <general>, the tube voltage of the x-ray tube bulb 113 is <50 (kVp)>, the tube current is <125 (mA)>, and the irradiation time is <50 (ms)>. Further, the radiographing controller 122 sets the driving conditions for the x-ray imaging apparatus 101 to the effect that the gain is <1>, and the driving method is <still image driving>. The radiographing controller 122 drives the x-ray imaging apparatus 101 and the x-ray generator apparatus 102 so as to prepare for the radiographing, and waits for the depression of the exposure button (not illustrated) by the engineer 110.

When the exposure button (not illustrated) is depressed by the engineer 110 and the exposure button is turned on, the radiographing controller 122 detects this (step S203).

Subsequently, the radiographing controller 122, based on the radiographing conditions set at step S202, drives the x-ray imaging apparatus 101 and the x-ray generator apparatus 102 so as to perform the capturing of the radiographed image (S204). Specifically, the x-ray is irradiated from the x-ray generator apparatus 102 under the irradiation conditions set at step S202, and the x-ray having transmitted the object 116 enters the x-ray imaging apparatus 101. At the x-ray imaging apparatus 101, the x-ray having transmitted the object 116 is received by the photoelectric conversion circuit unit 120, and based on the driving conditions set at step S202, the object image data radiographed by the driving circuit unit 121a and the readout circuit unit 121b is read by the control apparatus 109.

Subsequently, the image processing unit 105, based on a control from the radiographing controller 122, performs a basic image processing such as an offset correction for the object image data read from the x-ray imaging apparatus 101 (step S205).

Subsequently, the image processing unit 105, based on a control from the radiographing controller 122, performs the gain correction for the object image data processed at step S205 (step S206). Specifically, the image processing unit 105, first, extracts the image data for gain correction radiographed under the same conditions as the operation mode selected at step S201 from among the image memory 107 for gain correction. The image processing unit 105 divides the object image data by the extracted image data for gain correction or the like, thereby performing the gain correction. After that, the image processing unit 105 further performs a defect correction processing, spatial filtering processing, gradation processing, scattered radiation correction processing, spatial frequency processings of various types, and the like as occasion demands and according to the image processing conditions.

Subsequently, the image processing unit 105, based on a control from the radiographing controller 122, displays the object image data subjected to the image processing on a monitor (the operator interface 108 in the present embodiment) as the object image (step S207).

Here, in the case of the moving image radiographing, the x-ray is pulse-irradiated from the x-ray generator apparatus 102, and performs radiographing→readout→image processing→display renewal in real time.

As described above, by using the calibration table, the image for gain correction can be easily radiographed every operation mode. By using the same image for gain correction radiographed by the same operation mode at the radiographing time of the object image, the gain correction of the object image is performed, so that the object image having a high grade quality and no artifact can be obtained.

(Second Embodiment)

Next, a second embodiment of the present invention will be described.

The configuration of a radiation imaging system according to the second embodiment is the same as the radiation imaging system according to the first embodiment shown in FIGS. 1 and 2. Further, the processing in the radiographing operation of the radiation imaging system according to the second embodiment is the same as the processing in the radiographing operation of the radiation imaging system according to the first embodiment shown in FIG. 8. In the radiation imaging system according to the second embodiment, since the difference with the radiation imaging system according to the first embodiment is only about an acquisition processing of an image for gain correction, the description thereof only will be made in the following.

Figure 9:
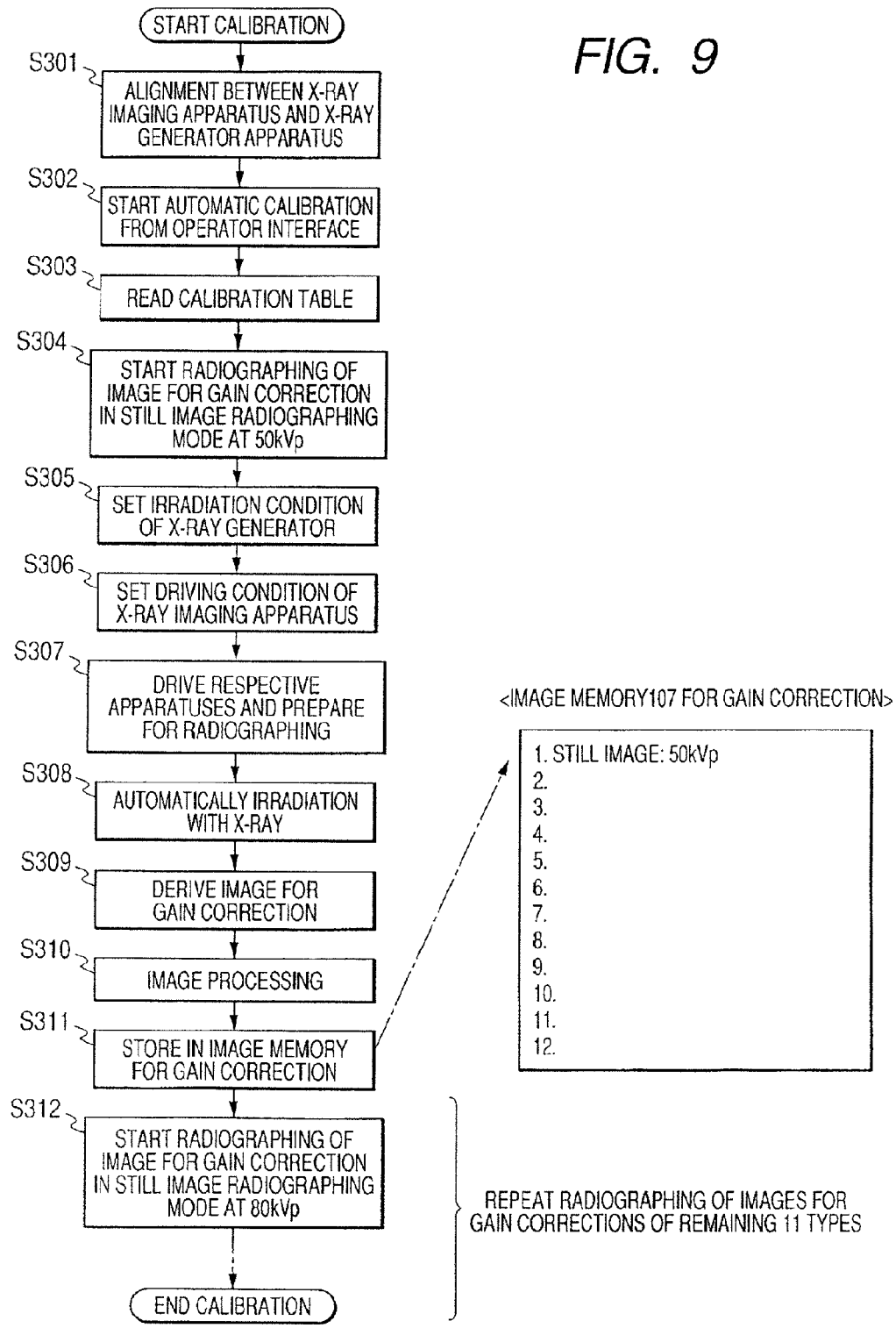
FIG. 9 is a flowchart showing the acquisition processing of the image for gain correction of the x-ray imaging system according to a second embodiment.
Figure 11:
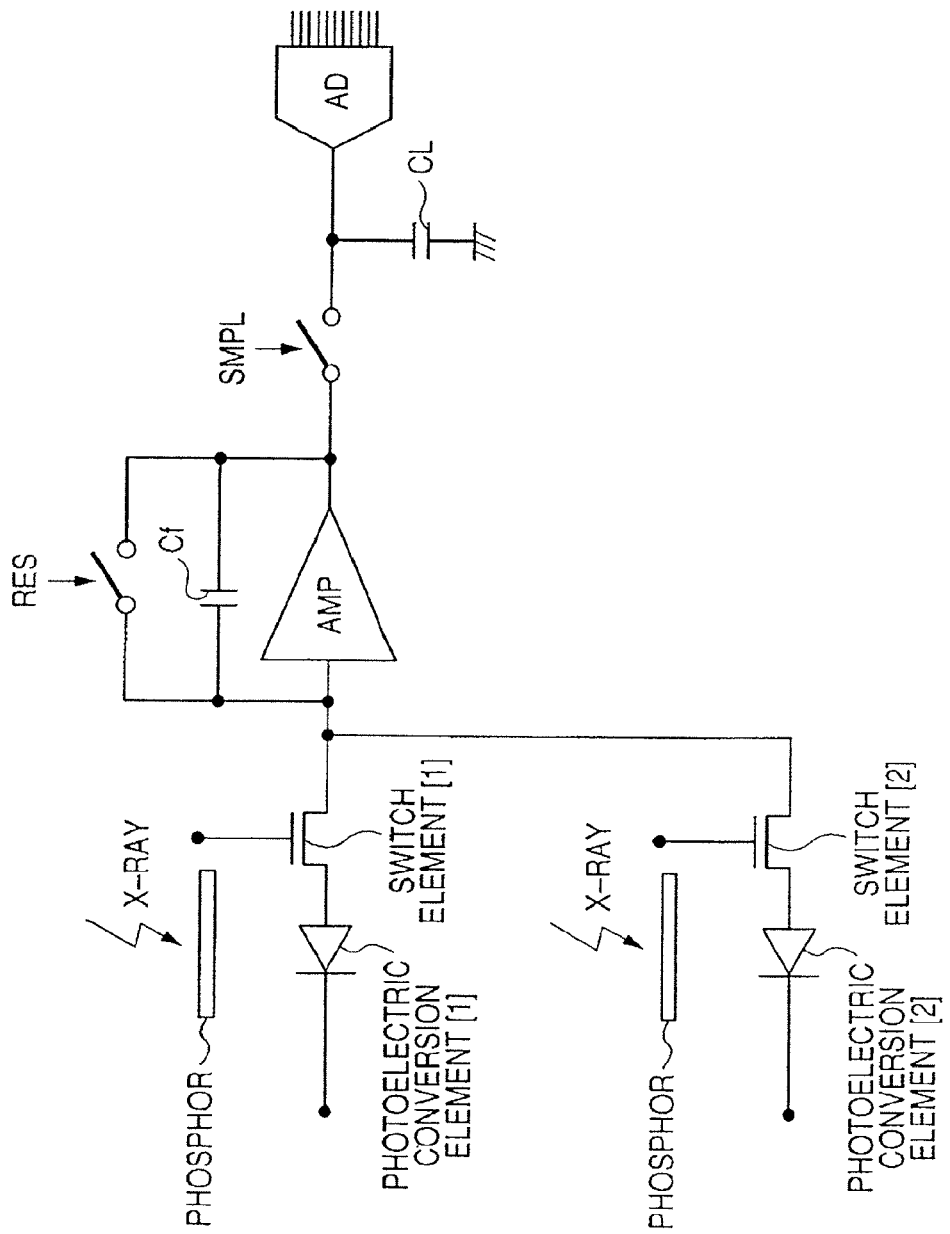
FIG. 11 is a schematic configuration view of a radiation imaging apparatus (x-ray imaging apparatus) used when an analogue signal is subjected to a pixel addition.
Figure 12:
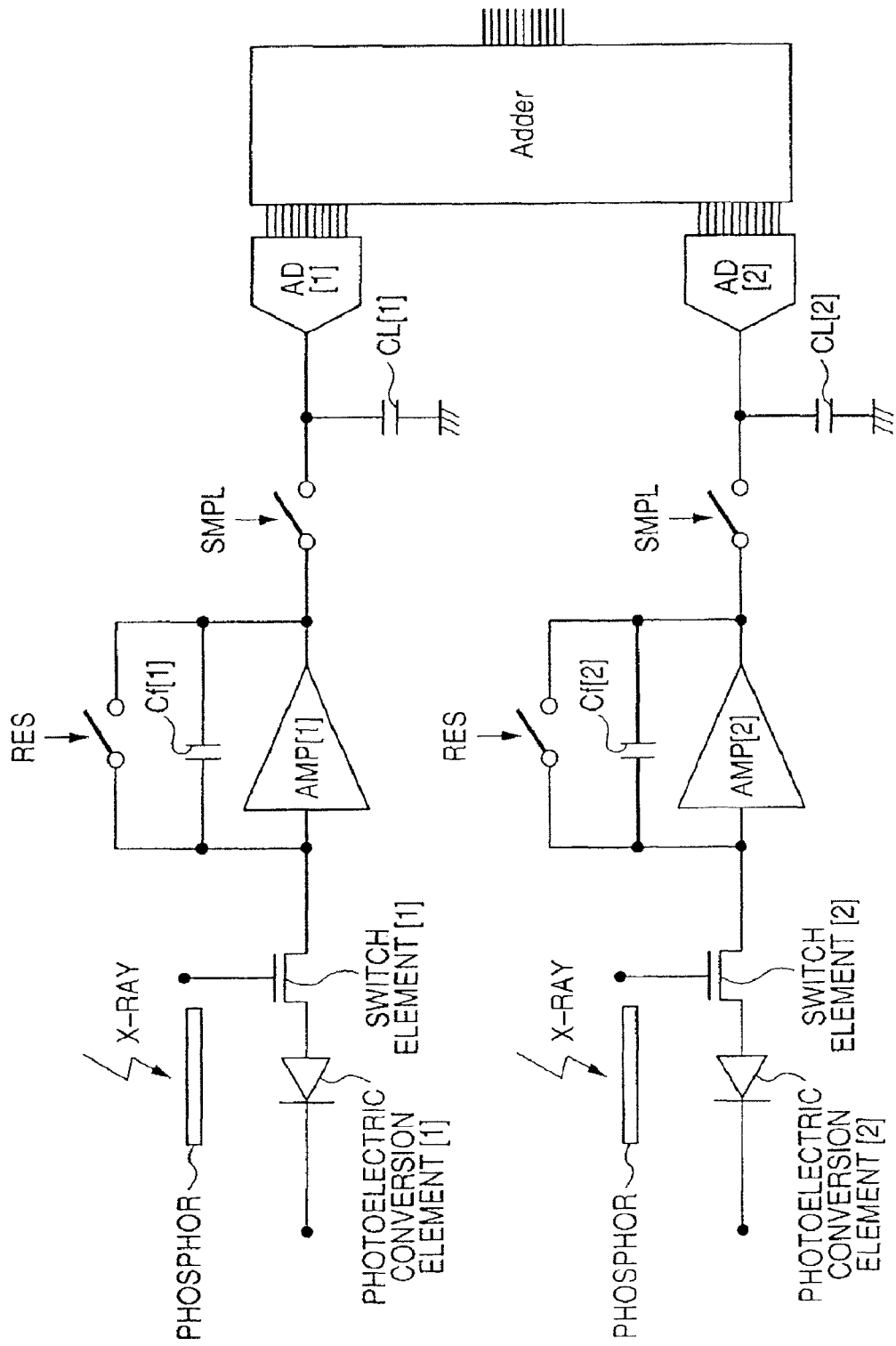
FIG. 12 is a schematic configuration view of a radiation imaging apparatus (x-ray imaging apparatus) used when a digital signal is subjected to a pixel addition.
Figure 13A:
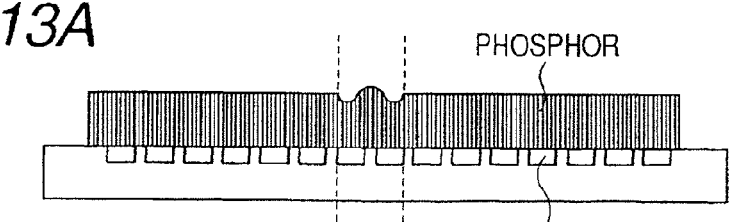
FIGS. 13A, 13B, 13C and 13D are views for describing an artifact.
Figure 13B:
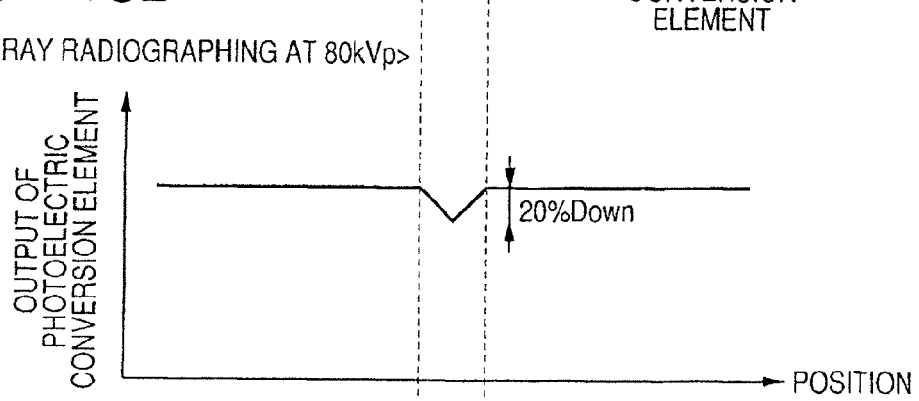
Figure 13C:
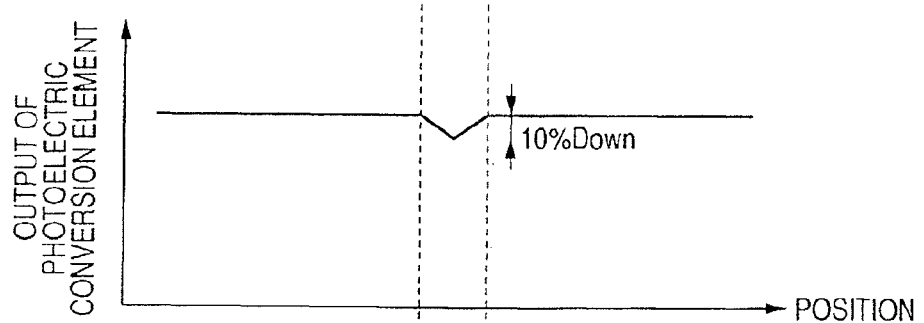
Figure 13D:
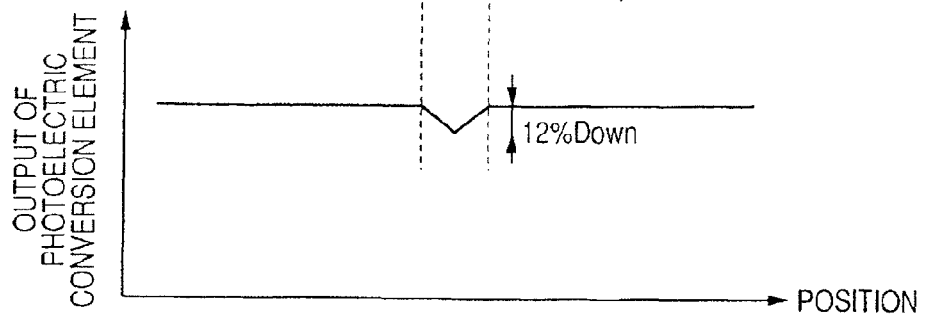

FIG. 9 is a flowchart showing the acquisition processing of the image for gain correction of the x-ray imaging system according to the second embodiment. That is, FIG. 9 is a flowchart showing the procedure in a calibration.

In the first embodiment, the mode was such that the calibration table is read, and radiographing conditions are set in the x-ray generator apparatus 102 and the x-ray imaging apparatus 101, and the exposure button (not illustrated) is depressed by the engineer 110 every operation mode, so that the radiographing of the image for gain correction is performed. On the other hand, in the second embodiment, the x-ray is automatically irradiated without the exposure button (not illustrated) depressed by the engineer 110, thereby to perform the radiographing of the image for gain correction.

Hereinafter, a description will be made based on the flowchart shown in FIG. 9.

First, similarly to the first embodiment, when starting the calibration, the engineer 110 operates an operator interface 108 and performs an alignment between the x-ray imaging apparatus 101 and the x-ray generator apparatus 102 (step S301). Subsequently, the engineer 110 instructs the start of an automatic calibration from the operator interface 108 (step S302).

A radiographing controller 122 having received the start of the automatic calibration from the operator interface 108 reads a calibration table stored in a calibration table memory 106 (step S303).

Subsequently, the radiographing controller 122, according to the order of the calibration table, first, performs a processing for starting the radiographing of the image for gain correction in the case where an x-ray tube bulb 113 is at a low tube voltage (50 kVp) by a still image radiographing mode shown in FIG. 3 (step S304). Here, when the radiographing of the image for gain correction is performed, it is performed in a state in which the object 116 does not exist.

Subsequently, the radiographing controller 122 performs the setting of the irradiation conditions (irradiation mode, tube voltage, tube current, and irradiation time) of the x-ray shown in the calibration table of FIG. 3 for the x-ray generator apparatus 102 (step S305).

Subsequently, the radiographing controller 122 performs the setting of the driving conditions (gain and driving method) shown in the calibration table of FIG. 3 for the x-ray imaging apparatus 101 (step S306).

Subsequently, the radiographing controller 122 sets the radiographing conditions for the x-ray imaging apparatus 101 and the x-ray generator apparatus 102, and after that, drives the x-ray imaging apparatus 101 and the x-ray generator apparatus 102 so as to prepare for the radiographing (step S307).

After having completed the radiographing preparation of step S307, the radiographing controller 122, based on the irradiation conditions set at step S305, allows the x-ray generator apparatus 102 to be driven and allows the x-ray to be automatically irradiated from the x-ray generator apparatus 102 (step S308).

Subsequently, the radiographing apparatus 122, based on the driving conditions set at step S306, allows the x-ray imaging apparatus 101 to be driven, and performs the capturing of the radiographed image (step S309). Specifically, in the x-ray imaging apparatus 101, first, the light converted by a wavelength converter 118 according to the x-ray from the x-ray generator apparatus 102 is received by a conversion circuit unit 120. Based on the driving conditions set at step S306, a driving circuit unit 121a and a readout circuit unit 121b are driven, so that the radiographing is performed, and the radiographed image data is read by a controller apparatus 109. This image data read by the controller apparatus 109 is an image data for gain correction used for a gain correction processing.

Subsequently, the image processing unit 105, based on a control from the radiographing controller 122, performs a basic image processing such as an offset correction for the image data for gain correction read from the x-ray imaging apparatus 101 (step S310). Subsequently, the image processing unit 105, based on a control from the radiographing control unit 122, stores the image data for gain correction subjected to the image processing in the image memory 107 for gain correction (step S311).

By going through the processings of these steps S304 to S311, the acquisition processing of the image for gain correction is performed in the case where the x-ray tube bulb 113 is at the low tube voltage (50 kVp).

Subsequently, the radiographing controller 122, according to the order of the calibration table, performs a processing for starting the radiographing of the image for gain correction by a still image radiographing mode shown in FIG. 3 in the case where the x-ray tube bulb 113 is at the medium tube voltage (80 kVp) (step S312). From then onward, according to the order of the calibration table of FIG. 3, the radiographing controller 122 repeats the same processing as the acquisition processing (steps S304 to S311) of the image for gain correction in the case where the x-ray tube bulb 113 is at the low tube voltage, so that the images for gain correction of the remaining eleven types shown in FIG. 3 can be obtained. As a result, the image data for gain correction every operation mode of a total twelve types shown in FIG. 3 can be stored in the image memory 107 for gain correction.

In general, the exposure of the x-ray is performed by the x-ray irradiation for the irradiation time set by the logical product of an exposure request signal from the radiographing controller (controller apparatus) and an exposure button signal, whereas, in the second embodiment, at the calibration time only, the x-ray is irradiated by the exposure request signal only from the radiographing controller 122. By so doing, when the calibration is once started, the engineer 110 needs not to do anything until the completion of the calibration. Hence, according to the second embodiment, the number of operation process steps can be reduced much more than the calibration operation in the first embodiment.

(Third Embodiment)

Next, a third embodiment of the present invention will be described.

In a radiation imaging system according to the third embodiment, the difference with the radiation imaging system of the first embodiment is only about information on a calibration table stored in a calibration table memory 106, and the description thereof only will be made in the following.

FIG. 10 is a view showing one example of the calibration table used for the x-ray imaging system according to the third embodiment.

The calibration table in the third embodiment shown in FIG. 10, as compared to that of the first embodiment shown in FIG. 3, is read as the driving conditions of the x-ray imaging apparatus 101, and is added with a cut off frequency (fc) of a low pass filter in the Amp of a readout circuit unit 121b.

Further, in the present embodiment, as the driving conditions in the x-ray imaging apparatus 101, other than those shown in FIG. 10, the mode forming a calibration table further including the voltage applied to the photoelectric conversion element and the voltage applied to the switch element can be applied.

In the still image radiographing mode, since the read time is slow, the cut off frequency fc is made low with the noise reduced small as shown in FIG. 10, and further, in the moving image radiographing mode, since the read time is fast, the cut off frequency fc is made high as shown in FIG. 10. Further, in addition to the time constant of the low pass filter, the bias conditions of the photoelectric conversion element are changed so as to change the sensitivity characteristics of the photoelectric conversion element, and the ON voltage of the switch element is changed so as to change the ON resistance of the switch element, so that the suitable gain correction can be performed at the still image radiographing time and the moving image radiographing time.

Each unit of FIGS. 1 and 2 comprising the radiation imaging system according to the above described each embodiment and each step of FIGS. 7 to 9 showing the driving method of the radiation imaging system can be realized by operating the program stored in the RAM and ROM or the like. This program and a computer readable storage medium recorded with this program are included in the present invention.

Specifically, the program, for example, is recorded in the storage medium such as CD-ROM or supplied to a computer through various transfer mediums. As the storage medium storing the program, in addition to CD-ROM, a flexible disc, hard disc, magnetic tape, magneto-optic disc, non-volatile memory card, and the like can be used. On the other hand, as the transfer medium of the program, a communication medium in the computer network (LAN, WAN such as Internet, wireless communication network, and the like) system for propagating and supplying the program information as a carrier wave can be used. Further, as the communication medium at this time, a wire circuit or a radio circuit such as an optical fiber can be cited.

Further, not only in the case where a computer executes a provided program so that the functions of the radiation imaging system according to each embodiment are not only realized, but also in the case where the functions of the radiation imaging system according to each embodiment are realized by the program in association with the OS (Operating system) operated inside the computer or other application soft and the like and as well as the case where all or a part of processings of the provided program are executed by the function expanding board or the function expanding unit so that the functions of the radiation imaging system according to each embodiment are realized, such program is also included in the present invention.

The present invention relates to the radiation imaging system for radiographing a radiation image of the object and its driving method, and in particular, it is suitably used for the radiation imaging system used for the diagnosis inside a hospital and the radiation imaging system used as a non-destructive inspection device for industrial purpose.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging system comprising:
   a radiation imaging unit for performing radiographing using radiation irradiated from a radiation generator that generates the radiation;
   a table storing unit for storing a table set with radiation conditions of the radiation of the radiation generator for an operation mode of a plurality of operation modes;
   a selecting unit for selecting an operation mode for performing radiographing from the plurality of operation modes;
   an image storing unit for storing image data of an image for gain correction obtained based on the radiation conditions set with the table in a state in which an object is not present to be radiographed and in which radiation is irradiated to said radiation imaging unit for the operation mode of the plurality of operation modes; and an image processing unit configured to perform a gain correction processing of object image data, wherein said image processing unit performs the gain correction processing of the object image data obtained based on the radiation condition set in the table of the operation mode selected by the selecting unit in a state in which the object is present to be radiographed using a corresponding image for gain correction extracted from said image storing unit based on the operation mode selected by the selecting unit.

2. The radiation imaging system according to claim 1, wherein said radiation imaging unit comprises a conversion unit having a plurality of pixels in a two dimensional matrix pattern, wherein each pixel comprises a conversion element for converting the radiation into an electric signal and a switch element for transferring the electric signal of said conversion element, and a readout unit for reading the electric signal from the conversion unit.

3. The radiation imaging system according to claim 2, further comprising a control unit driving the radiation imaging unit based on driving conditions set in the table of the operation mode selected by the selecting unit.

4. The radiation imaging system according to claim 3, wherein the driving conditions of said radiation imaging unit set in the table include at least one of: an amplification factor of the electric signal in said readout unit, a number of additions in the electric signal of said pixel when reading the electric signal from said conversion unit, voltage applied to said conversion element, voltage applied to said switch element, and the cutoff frequency of a low pass filter in said readout unit.

5. The radiation imaging system according to claim 2, wherein said conversion element includes a photoelectric conversion element, and said photoelectric conversion element has amorphous silicon as its primary material.

6. The radiation imaging system according to claim 5, wherein said photoelectric conversion element includes a MIS-type photoelectric conversion element or a PIN-type photoelectric conversion element.

7. The radiation imaging system according to claim 5, further comprising a wavelength converter for converting a wavelength of the radiation, and wherein said photoelectric conversion element receives incident light produced from the radiation by said wavelength converter.

8. The radiation imaging system according to claim 2, wherein said conversion element has a function to absorb the radiation and directly convert the radiation into the electric signal, and said conversion element has as its primary material a material selected from the group consisting of amorphous selenium, gallium arsenide, mercuric iodide, lead iodide, and cadmium telluride.

* * * * *